US008394601B2

(12) United States Patent
Klein et al.

(10) Patent No.: US 8,394,601 B2
(45) Date of Patent: Mar. 12, 2013

(54) PEPTIDE BIOMARKERS PREDICTIVE OF RENAL FUNCTION DECLINE AND KIDNEY DISEASE

(75) Inventors: Jon B. Klein, Louisville, KY (US); Michael Merchant, Louisville, KY (US); Grzegorz Boratyn, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 13/234,756

(22) Filed: Sep. 16, 2011

(65) Prior Publication Data

US 2012/0009606 A1    Jan. 12, 2012

Related U.S. Application Data

(63) Continuation of application No. 12/234,401, filed on Sep. 19, 2008, now Pat. No. 8,039,227.

(60) Provisional application No. 60/974,002, filed on Sep. 20, 2007, provisional application No. 61/050,521, filed on May 5, 2008.

(51) Int. Cl.
*C07K 7/00* (2006.01)
*G01N 33/53* (2006.01)
*H01J 49/26* (2006.01)
*H01J 49/40* (2006.01)

(52) U.S. Cl. ....... 435/7.92; 530/326; 530/327; 530/328; 530/329; 530/387.1; 436/501

(58) Field of Classification Search .......................... None
See application file for complete search history.

(56) References Cited

U.S. PATENT DOCUMENTS

| 7,510,842 B2 * | 3/2009 | Podust et al. ................. 435/7.1 |
| 7,972,770 B2 | 7/2011 | Tempst et al. |
| 2004/0101874 A1 | 5/2004 | Ghosh et al. |
| 2007/0050146 A1 | 3/2007 | Bentwich et al. |
| 2007/0105133 A1 | 5/2007 | Clarke et al. |
| 2007/0111245 A1 | 5/2007 | Thadhani et al. |

OTHER PUBLICATIONS

CDC, Burrows et al., "Incidence of end-stage renal disease among persons with diabetes—United States, 1990-2002," MMWR Morb Mortal Wkly Rep. 54, 2005, pp. 1097-1100.
Morrison et al., "Apo2L/TRAIL induction and nuclear translocation of inositol hexakisphosphate kinase 2 during IFN-beta-induced apoptosis in ovarian carcinoma," Biochem J., 385, 2005, pp. 595-603.
Morrison et al., "Effect of inositol hexakisphosphate kinase 2 on transforming growth factor beta-activated kinase 1 and NF-kappaB activation," J Biol Chem., 282, 2007, pp. 15349-15356.
Spiro et al., "Studies on the biosynthesis of the hydroxylysine-linked disaccharide unit of basement membranes and collagens. III. Tissue and subcellular distribution of glycosyltransferases and the effect of various conditions on the enzyme levels, " J Biol Chem., 246, 1971, pp. 4919-4925.
Striker et al., "Diabetic nephropathy: molecular analysis of extracellular matrix and clinical studies update," Nephrol Dial Transplant., 11 Suppl, 5, 1996, pp. 58-61.
Kanetsuna et a. "Characterization of diabetic nephropathy in a transgenic model of hypoinsulinemic diabetes," Am J Physiol Renal Physiol., 291, 2006, pp. F1315-F1322.
Akahori et al., "Tranilast prevents the progression of experimental diabetic nephropathy through suppression of enhanced extracellular matrix gene expression," J Pharmacol Exp Ther., 314, 2005, pp. 514-521.
Benigni et al., "Add-on anti-TGF-beta antibody to ACE inhibitor arrests progressive diabetic nephropathy in the rat," J Am Soc Nephrol., 14, 2003, pp. 1816-1824.
Guha et al., "Specific down-regulation of connective tissue growth factor attenuates progression of nephropathy in mouse models of type 1 and type 2 diabetes," Faseb J., 21, 2007, pp. 3355-3368.
Nerlich et al., "Immunohistochemical localization of extracellular matrix components in human diabetic glomerular lesions," Am J Pathol., 139, 1991, pp. 889-899.
Watanabe et al., "Serum or urinary concentration of type IV collagen in diabetics," J Diabet Complications., 5, 1991, pp. 191-192.
Yagame et al., "Significance of urinary type IV collagen in patients with diabetic nephropathy using a highly sensitive one-step sandwich enzyme immunoassay," J Clin Lab Anal., 11, 1997, pp. 110-116.
Iijima et al., "Follow-up study on urinary type IV collagen in patients with early stage diabetic nephropathy," J Clin Lab Anal., 12, 1998, pp. 378-382.
Cohen et al., "Increased collagen IV excretion in diabetes. A marker of compromised filtration function," Diabetes Care, 24, 2001, pp. 914-918.
Ellis et al., "Urinary measurement of transforming growth factor-beta and type IV collagen as new markers of renal injury: application in diabetic nephropathy," Clin. Chem., 44, 1998, pp. 950-956.
Weissinger et al., "Proteomic patterns established with capillary electrophoresis and mass spectrometry for diagnostic purposes," Kidney Int., 65, 2004, pp. 2426-2434.
Mischak et al., "Proteomic analysis for the assessment of diabetic renal damage in humans," Clin Sci (Lond)., 107, 2004, pp. 485-495.
Rossing et al., "Impact of diabetic nephropathy and angiotensin II receptor blockage on urinary polypeptide patterns," Kidney Int., 68, 2005, pp. 193-205.
Decramer et al., "Predicting the clinical outcome of congenital unilateral ureteropelvic junction obstruction in newborn by urinary proteome analysis," Nat Med., 12, 2006, pp. 398-400.
Wittke et al., "Determination of peptides and proteins in human urine with capillary electrophoresis-mass spectrometry, a suitable tool for the establishment of new diagnostic markers," J Chromatogr A., 1013, 2003, pp. 173-181.

(Continued)

*Primary Examiner* — Julie Ha
(74) *Attorney, Agent, or Firm* — Stites & Harbison PLLC; Terry L. Wright

(57) ABSTRACT

Methods and kits are provided for diagnosing a kidney disease, or the risk thereof, in a subject. The methods include determining an amount of at least one peptide biomarker disclosed herein in a biological sample from the subject and comparing the amount of the at least one peptide in the sample with a control level, wherein if the amount determined is different than the control level, the subject is diagnosed as having, or at an increased risk of developing, the kidney disease.

12 Claims, 5 Drawing Sheets

OTHER PUBLICATIONS

Fiedler et al., "Standardized peptidome profiling of human urine by magnetic bead separation and matrix-assisted laser desorption/ionization time-of-flight mass spectrometry," Clin Chem., 53, 2007, pp. 421-428.

Giorgino et al., "Factors associated with progression to macroalbuminuria in microalbuminuric Type 1 diabetic patients: the EURODIAB Prospective Complications Study," Diabetologia., 47, 2004, pp. 1020-1028.

Perkins et al., "Regression of microalbuminuria in type 1 diabetes," N. Engl. J. Med., 348, 2003, pp. 2285-2293.

Araki et al., "Factors associated with frequent remission of microalbuminuria in patients with type 2 diabetes," Diabetes, 54, 2005, pp. 2983-2987.

Perkins et al., "Microalbuminuria and the risk for early progressive renal function decline in type 1 diabetes," J Am Soc Nephrol., 18, 2007, pp. 1353-1361.

Perkins et al., "Detection of renal function decline in patients with diabetes and normal or elevated GFR by serial measurements of serum cystatin C concentration: results of a 4-year follow-up study," J.Am.Soc.Nephrol., 16, 2005, pp. 1404-1412.

Brehm et al., "Intracellular localization of human inositol 1, 3, 4, 5, 6-pentakisphosphate 2-kinase," Biochem J., 408 (3), 2007, pp. 335-345.

Anderson et al., "RNA granules," J Cell Biol., 172, 2006, pp. 803-808.

Verbsky et al., "The synthesis of inositol hexakisphosphate. Characterization of human inositol 1, 3, 4, 5, 6-pentakisphosphate 2-kinase," J Biol Chem., 277, 2002, pp. 31857-31862.

Verbsky et al., "The pathway for the production of inositol hexakisphosphate in human cells," J Biol Chem., 280, 2005, pp. 1911-1920.

Alcazar-Roman et al., "Inositol hexakisphosphate and Gle1 activate the DEAD-box protein Dbp5 for nuclear mRNA export," Nat Cell Biol., 8, 2006, pp. 711-716.

Wang et al., "Apical junctional complexes and cell polarity," Kidney Int., 72, 2007, pp. 1448-1458.

Kiener et al., "Tjp3/zo-3 is critical for epidermal barrier function in zebrafish embryos," Dev Biol., 316, 2008, pp. 36-49.

Sharma et al., "Adiponectin regulates albuminuria and podocyte function in mice," J Clin Invest., 118(5), 2008, pp. 1645-1656.

Tan et al., "Targeted deletion of B2-kinin receptors protects against the development of diabetic nephropathy," Am J Physiol Renal Physiol., 293(4), 2007, pp. F1026-F1035.

Pavkov et al., "Increasing incidence of proteinuria and declining incidence of end-stage renal disease in diabetic Pima Indiana," Kidney Int., 70, 2006, pp. 1840-1846.

Hovind et al., "Decreasing incidence of severe diabetic microangiopathy in type 1 diabetes," Diabetes Care, 26, 2003, pp. 1258-1264.

Hovind et al., "Predictors for the development of microalbuminuria and macroalbuminuria in patients with type 1 diabetes: inception cohort study," BMJ., 328, 2004, p. 1105.

ISA/US, International Search Report and Written Opinion of related International Application No. PCT/US08/77091, mailed Feb. 13, 2009.

Merchant et al, "Proteomics and diabetic nephropathy," Current Diabetes Reports, Dec. 1, 2005, vol. 5, No. 6, pp. 464-469, Current Science, Philadelphia, PA, US.

Rao et al., "Proteomic identification of urinary biomarkers of diabetic nephropathy," Diabetes Care, Mar. 1, 2007, vol. 30, No. 3, pp. 629-637, American Diabetes Association, Alexandria, VA, US.

Kiga et al., "Expression patterns of plasma proteins in spontaneously diabetic rats after oral administration of a Kampo medicine, Hachimi-jio-gan, using SELDI ProteinChip platform, "Biological & Pharmaceutical Bulletin, Jun. 2005, vol. 28, No. 6, pp. 1031-1037.

Kim et al., "Proteome analysis of serum from type 2 diabetics with nephropathy," Journal of Proteome Research, Feb. 2007, vol. 6, No. 2, pp. 735-743.

Willis et al., "Molecular cloning of translocation t(1;14)(q21;q32) defines a novel gene (BCL9) at chromosome 1q21," Blood, Mar. 15, 2008, vol. 91, No. 6, pp. 1873-1881, American Society of Hematology, US.

Merchant et al., "Urinary Peptidome May Predict Renal Function Decline in Type 1 Diabetes and Microalbuminuria," Journal of the American Society of nephrology, Sep. 2009, vol. 20, No. 9, pp. 2065-2074.

European Patent Office, Supplementary European Search Report for corresponding European patent application No. 08832096.5, completed Jan. 14, 2011.

* cited by examiner

PEPTIDE BIOMARKERS PREDICTIVE OF RENAL FUNCTION DECLINE AND KIDNEY DISEASE

RELATED APPLICATIONS

The present application is a continuation application of U.S. application Ser. No. 12/234,401, which claims the benefit of U.S. Provisional Patent Application Ser. No. 60/974,002 filed Sep. 20, 2007 and U.S. Provisional Patent Application Ser. No. 61/050,521, filed May 5, 2008; the disclosures of each of which are incorporated herein by reference in their entireties.

GOVERNMENT INTEREST

This invention was made with U.S. Government support under Grant Nos. R01-DK41526 and RO1-DK067638-02 awarded by National Institutes of Health. The U.S. Government has certain rights in this invention.

TECHNICAL FIELD

The presently disclosed subject matter relates to methods for diagnosing a kidney disease in a subject. In particular, the presently disclosed subject matter relates to methods for diagnosing a kidney disease in a subject by determining an amount of one or more peptide biomarkers in a biological samples from the subject.

BACKGROUND

Diabetic nephropathy (DN) is a kidney disease that is a severe late complication of type 1 diabetes (T1D), which frequently requires renal replacement therapy. The primary diagnostic test to identify patients with T1D at risk for progressive renal dysfunction leading to DN has been microalbuminuria (MA) (1, 2). However, the predictive value of MA is now questioned: First, only a fifth of patients with MA will progress to proteinuria (3); second, a large proportion of patients with MA can revert to normoalbuminuria (4-6); and third, many patients at the onset of MA have begun to experience early renal function decline (ERFD) (7, 8). These findings have called into question the previous paradigm of DN in T1D, in which the finding of MA conveyed a high risk of progressive renal dysfunction and support a new model in which a subset of those with MA develop progressive ERFD. This change in our understanding of diabetic renal disease also is indicative of our incomplete understanding of the mechanisms of ERFD, a process that takes place while measured renal function is still in the normal or even elevated range. These findings emphasize the need for the development of biomarkers to diagnose kidney disease such as ERFD in those with MA.

Accordingly, there is an unmet need for new biomarkers and methods of using same for diagnosing kidney disease.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments of the presently-disclosed subject matter, a method for diagnosing a kidney disease, or the risk thereof, in a subject is provided. In some embodiments, the method comprises determining an amount of at least one peptide of Table 1 (e.g., SEQ ID NOS: 60-79), Table 2 (e.g., SEQ ID NOS: 80-118), or both in a biological sample from the subject. The method then comprises comparing the amount of the at least one peptide in the sample with a control level, wherein if the amount determined is different than the control level, the subject is diagnosed as having, or at an increased risk of developing, the kidney disease.

In other embodiments of the presently-disclosed subject matter, a method for determining treatment efficacy and/or progression of a kidney disease in a subject is provided. In some embodiments, the method comprises determining an amount of at least one peptide of Table 1 (e.g., SEQ ID NOS: 60-79), Table 2 (e.g., SEQ ID NOS: 80-118), or both in a first biological sample collected from the subject at a first time point; determining an amount of the at least one peptide of Table 1 (e.g., SEQ ID NOS: 60-79), Table 2 (e.g., SEQ ID NOS: 80-118), or both in a second biological sample from the subject at a second time point; and comparing the amounts of the at least one peptide in the first and second samples, wherein a change in the amounts of the at least one peptide from the first and second samples is correlated with determining treatment efficacy and/or progression of the kidney disease in the subject. In some embodiments, the first time point is prior to initiation of a treatment for the kidney disease and the second time point is after initiation of the treatment. In other embodiments, the first time point is prior to onset of the kidney disease and the second time point is after onset of the kidney disease.

In some embodiments of the methods disclosed herein, determining the amount of the at least one peptide comprises determining the amount of the at least one peptide in the sample using mass spectrometry (MS) analysis, immunoassay analysis, or both. The MS analysis can comprise in some embodiments matrix-assisted laser desorption/ionization (MALDI) time-of-flight (TOF) MS analysis or electrospray ionization (ESI) MS. The MALDI-TOF MS analysis can be direct-spot MALDI-TOF or liquid chromatography MALDI-TOF mass spectrometry analysis. In some embodiments, the immunoassay analysis comprises an enzyme-linked immunosorbent assay (ELISA).

In some embodiments, the at least one peptide is a plurality of peptides. Further, in some embodiments, the biological sample is a urine sample and the at least one peptide is at least one peptide selected from Table 1 (e.g., SEQ ID NOS: 60-79). In other embodiments, the biological sample is a blood sample or a plasma sample and the at least one peptide is at least one peptide selected from Table 2 (e.g., SEQ ID NOS: 80-118).

In some embodiments, the subject is human. In some embodiments, the subject is a diabetic subject. In some particular embodiments, the kidney disease is diabetic nephropathy.

In further embodiments of the presently-disclosed subject matter, an antibody or fragment thereof is provided that specifically recognizes a peptide of Table 1 (e.g., SEQ ID NOS: 60-79) or Table 2 (e.g., SEQ ID NOS: 80-118), a peptide associated with a peptide of Table 1 (e.g., SEQ ID NOS: 60-79) or Table 2 (e.g., SEQ ID NOS: 80-118), or both. In some embodiments, the antibody is a monoclonal antibody.

In still other embodiments of the presently-disclosed subject matter, a kit for detecting a kidney disease, or a risk thereof, in a subject is provided. The kit comprises one or more antibodies disclosed herein that specifically recognizes a peptide of Table 1 (e.g., SEQ ID NOS: 60-79) or Table 2 (e.g., SEQ ID NOS: 80-118), a peptide associated with a peptide of Table 1 (e.g., SEQ ID NOS: 60-79) or Table 2 (e.g., SEQ ID NOS: 80-118), or both. The kit can comprise instructions for using the kit. In some embodiments, the antibody is bound to a substrate. In some embodiments, the kit comprises a plurality of different antibodies.

Accordingly, it is an object of the presently disclosed subject matter to provide peptide biomarkers predictive of kidney disease and methods for using same. This object is achieved in whole or in part by the presently disclosed subject matter.

An object of the presently disclosed subject matter having been stated hereinabove, and which is achieved in whole or in part by the presently disclosed subject matter, other objects and advantages will become evident to those of ordinary skill in the art after a study of the following description of the presently disclosed subject matter, figures, and non-limiting examples.

DETAILED DESCRIPTION

Figure 1:
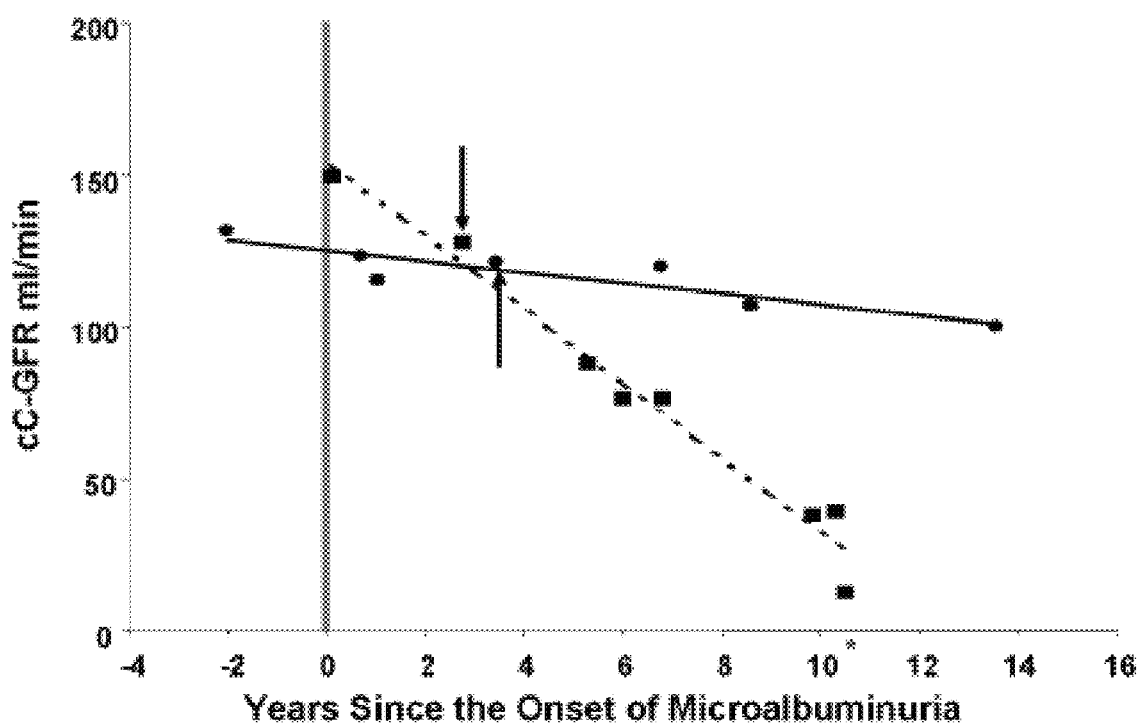
FIG. 1 is a graph showing serial estimates of representative examples of patients with early renal function decline (hatched line) and with stable renal function (solid line). The solid line represents the annual linear change in cC-GFR for a representative control individual in which the loss of renal function did not exceed the fixed threshold for case definition of ~3.3%/year. The hatched line represents the annual linear change for a case with early renal function decline. The mean slope for the control subject was ~1.4%/year while the mean slope for the case was ~12.0%/year. Beginning with a cC-GFR value of 152 ml/min, within 10 years this latter individual reached end-stage renal disease (*). Arrows indicate examinations from which urine samples were used for peptide component analysis. cC-GFR, glomerular filtration rate estimated by 100/serum cystatin C (in mg/ml).

The details of one or more embodiments of the presently disclosed subject matter are set forth in the accompanying description below. Other features, objects, and advantages of the presently disclosed subject matter will be apparent from the detailed description, Appendix, and claims. All publications, patent applications, patents, and other references mentioned herein are incorporated by reference in their entirety. Some of the polynucleotide and polypeptide sequences disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein. In case of conflict, the present specification, including definitions, will control.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a cell" or "a virus" includes a plurality of such cells or viruses, respectively, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached exemplary claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Earlier identification and treatment of kidney disease can result in reducing or even preventing kidney disease progression and improving disease treatment prognosis. Presently, diagnosis of kidney disease usually occurs after significant damage has already resulted. Higher degrees of previous kidney damage at diagnosis limit the efficacy of kidney function preservation therapies and result in higher disease progression rates. Thus, a biomarker of kidney damage that is able to indicate the presence of both early damage and identify patients at an increased risk of progressive disease would favorably impact kidney disease diagnosis and treatment. Desirably, the biomarker would indicate renal damage prior to the current indicators of kidney dysfunction, be available non-invasively, and be easily interpretable.

Current markers of kidney disease and kidney disease progression include serum creatinine and urinary protein concentration, including microalbuminuria (MA). The slope of the decrease in glomerular filtration rate (GFR) has been demonstrated to predict the timing of end-stage renal disease (ESRD), and the level of proteinuria has been shown to correlate with kidney disease progression rates. These biomarkers of kidney disease provide some utility; however, their ability to recognize early kidney disease is limited. Recent studies have demonstrated that MA does not correlate well with the development of kidney disease in more than 30% of patients with Type I diabetes (T1DM). Further, studies also demonstrate that 20-30% of patients with Type 2 diabetes (T2DM) progress to chronic kidney disease in the absence of MA. In addition, serum creatinine concentration is recognized as an unreliable measure of kidney function because it is dependent on age, gender, race, muscle mass, weight, and various medications. Correct interpretation of kidney function based on serum creatinine requires complex formulas that are not routinely employed by practicing healthcare providers.

Thus, there is presently an unmet need for diagnostic and prognostic biomarkers of early and/or progressive kidney disease that become "positive" prior to or at the earliest point that kidney damage begins to occur. This "subclinical" kidney damage recognition would occur prior to or in the absence of a rise in serum creatinine, the development of urinary creatinine, or MA. A benefit that identification of subclinical kidney damage would confer is the ability to initiate early interventions to promote kidney function preservation. The presently disclosed subject matter is based, in part, on the discovery that proteomic profiling can be used to identify biomarkers in biological samples, such as for example urine, blood or plasma, that are associated with development of kidney disease, in some instances before any clinically identifiable alteration in renal function (e.g., glomerular filtration rate), serum creatinine concentration, or urine albumin excretion (e.g., MA) occurs.

In some embodiments of the presently disclosed subject matter, a method for diagnosing a kidney disease, or the risk for development thereof, in a subject is provided. In some embodiments, the method comprises obtaining a biological sample from the subject and determining an amount (including a qualitative determination of the presence or absence) of at least one peptide biomarker associated with kidney disease, such as for example one or more peptides set forth in Table 1 (e.g., SEQ ID NOS: 60-79) or Table 2 (e.g., SEQ ID NOs: 80-118). The method can further comprise comparing the amount of the at least one peptide in the sample with a control level. If the amount determined from the sample differs from (e.g., is greater than or less than) the control level, the subject can be diagnosed as having, or being at an increased risk of developing, the kidney disease.

TABLE 1

Urinary Peptide Biomarkers of Kidney Disease

| SEQ ID NO. | Observed Mass* (m/z, z = +1) | Urinary Abundance Change with progressive RFD | Candidate Parent Protein** | Swiss Prot Accession No. |
|---|---|---|---|---|
| | 731.286 | Decreased | | |
| | 736.238 | Increased | B-cell lymphoma 9 protein | O00512 |
| 1 (60) | | Peptide Sequence | P.GNPGNM(ox)M.F | |
| | 740.273 | Decreased | | |
| | 764.288 | Increased | | |
| | 766.437 | Increased | | |
| | 775.291 | Decreased | | |
| | 805.408 | Increased | B-cell lymphoma 9 protein | O00512 |
| 2 (61) | | Peptide Sequence | S.STPLPPDG.T | |
| | 811.388 | Increased | | |
| | 983.534 | Increased | zona occludens 3 | Q2VPE5 |
| 3 (62) | | Peptide Sequence | G.VSSQNLSLN.D | |
| | 1036.135 | Increased | | |
| | 1067.423 | Decreased | | |
| | 1126.515 | Increased | Ubiquilin-2 | Q9UHD9.2 |
| 4 (63) | | Peptide Sequence | I.GPIGPIGPTGPAA.P | |
| | 1165.525 | Decreased | eIF4y (eukaryotic translation initiation factor 4 gamma) | Q04637 |
| 5 (64) | | Peptide Sequence | I.IADRPGLPGPE.H | |
| | 1190.638 | Increased | FAT tumor suppressor 2 | Q9NYQ8 |

TABLE 1-continued

Urinary Peptide Biomarkers of Kidney Disease

| SEQ ID NO. | Observed Mass* (m/z, z = +1) | Urinary Abundance Change with progressive RFD | Candidate Parent Protein** | Swiss Prot Accession No. |
|---|---|---|---|---|
| 6 (65) | | Peptide Sequence | S.PEFQQHLYE.A | |
| | 1202.535 | Increased | alpha-1 (IV) collagen | P02462 |
| 7 (66) | | Peptide Sequence | L.PGPKGSPGSVGLK.G | |
| | 1202.553 | Decreased | alpha-5 (IV) collagen | P29400 |
| 8 (67) | | Peptide Sequence | P.GLPGP(OH)PGPMDP(OH)N.L | |
| | 1216.571 | Decreased | | |
| | 1399.876 | Decreased | | |
| | 1512.675 | Increased | alpha-1 (III) collagen | P02461 |
| 9 (68) | | Peptide Sequence | G.SP(OH)GSNGAP(OH)GQRGEP(OH)GP.Q | |
| | 1650.846 | Increased | Ubiquitin protein ligase URE-B1 | Q7Z6Z7 |
| 10 (69) | | Peptide Sequence | T.KLKKTPTEAPADCRA.L | |
| | 1717.821 | Increased | | |
| | 1819.831 | Increased | alpha-1 (III) collagen | P02461 |
| 11 (70) | | Peptide Sequence | Q.GLP(OH)GTGGP(OH)P(OH)GENGKPGEPGP(OH).K | |
| | 1838.831 | Increased | Inositol-1,3,4,5,6-pentakisphosphate 2-kinase | Q9H8X2 |
| 12 (71) | | Peptide Sequence | E.WGYHGEGNK(GlyGly)SLVVAHA.Q | |
| | 1841.846 | Decreased | | |
| | 2097.888 | Decreased | alpha-1 (I) collagen | P02452 |
| 13 (72) | | Peptide Sequence | N.GAP(OH)GNDGAKGDAGAP(OH)GAP(OH)GSQGAP(OH)G.L | |
| | 2196.082 | Decreased | alpha-1 (IV) collagen | P02462 |
| 14 (73) | | Peptide Sequence | S.PGP(OH)WGAP(OH)GLP(OH)GEKGDHGFPGSS.G | |
| | 2280.788 | Decreased | alpha-1 (III) collagen | P02461 |
| 15 (74) | | Peptide Sequence | G.KNGEYGP(OH)QGPPGPTGPGGDK(OH)GDT.G | |
| | 2293.157 | Decreased | | |
| | 2315.085 | Decreased | alpha-1 (V) collagen | P20908 |
| 16 (75) | | Peptide Sequence | G.PKGRGGPNGDPGPLGPP(OH)GEKGK(OH)LG.V | |
| | 2339.108 | Decreased | ITI heavy chain H4 | Q14624 |
| 17 (76) | | Peptide Sequence | L.LSDPEQGVEVTGQYEREKAGF.S | |
| | 2378.177 | Decreased | alpha-1 (I) collagen | P02452 |
| 18 (77) | | Peptide Sequence | P.GKNGDDGEAGKP(OH)GRP(OH)GERGPP(OH)GPQ.G | |
| | 2413.091 | Decreased | Fc alpha receptor isoform e | P24071 |
| 19 (78) | | Peptide Sequence | Q.CQAIREAYLTQLMIIK(OH)N(OH)STY.R | |
| | 3266.384 | Decreased | alpha-1 (III) collagen | P02461 |
| 20 (79) | | Peptide Sequence | P.AGPPGP(OH)P(OH)GPPGTSGHP(OH)GSP(OH)GSP(OH)GYQGP(OH)P(OH)GEPGQAGP.S | |

*Mass Accuracy ± 150 ppm
**First and last amino acids in the presented sequence are separated from the candidate peptide sequence by periods. The amino acid sequence contained within these bracketing amino acids (SEQ ID NOS: 60-79) is the proposed amino acid sequence for the peptide biomarker. ( ) denotes a posttranslational modification of the preceding amino acid. (OH) denotes hydroxylation. (GlyGly) denotes a glycine-glycine modification to the lysine side chain epsilon amino group.

TABLE 2

Plasma Peptide Biomarkers of Kidney Disease

| Protein Entry | SEQ ID NO. | Observed Mass* (m/z, z = +1) | Parent Protein | Peptide Sequence** | Gen Info. Accession (gi\|) No. | Expression with RFD$ | Peptide Selection Method# |
|---|---|---|---|---|---|---|---|
| 1 | | | Fibrinogen | | 11761629 | | |
| | 21 (80) | 1536.701 | | T.ADSGEGDFLAEGGGVR.G | | I | T, F (>) |
| | 22 (81) | 1558.679 | | T.ADSGEGDFLAEGGGVR.G (DE Sodiation) | | I | F (>) |
| | 23 (82) | 2861.295 | | K.MADEAGSEADHEGTHSTKRGHAKSRPV.R | | D | T |
| | 24 (83) | 2877.326 | | K.M(ox)ADEAGSEADHEGTHSTKRGHAKSRPV.R | | D | T |
| 2 | | | HMW Kininogen | | 225724 | | |
| | 25 (84) | 757.409 | | K.RPPGFSP.F | | I | T, C$^\&$, F (>) |
| | 26 (85) | 904.476 | | K.RPPGFSPF.R | | I | T, F (>) |
| | 27 (86) | 920.479 | | K.RPP(OH)GFSPF.R | | I | T |
| | 28 (87) | 920.479 | | K.RPPGFSP(OH)F.R | | I | T |
| | 29 (88) | 1060.584 | | K.RPPGFSPFR.K | | I (m) | T |
| | 30 (89) | 1092.551 | | K.RPP(OH)GFSP(OH)FR.K | | I | T, C$^\&$ |
| | 31 (90) | 1055.498 | | H.DWGHEKQR.K | | D | F (<) |
| | 32 (91) | 1943.887 | | H.NLGHGHKHERDQGHGHQ.R | | I | F (>) |
| 3 | | | Inter-alpha trypsin inhibitor heavy chain related protein | | 4096840 | | |
| | 33 (92) | 976.522 | | M.NFRPGVLSS.R | | I | F (>) |
| | 34 (93) | 1786.844 | | L.GLPGPPDVPDHAAYHPF.R | | I | T |
| | 35 (94) | 1675.795 | | P.GPPDVPDHAAYHPFR.R | | I (m) | T |
| | 36 (95) | 842.420 | | D.HAAYHPF.R | | D | F (<) |
| 4 | | | Complement Component C4A | | 179674 | | |
| | 37 (96) | 1052.496 | | Q.DEGAEPLKQ.R (Gamma-carboxyl; E); (Sodiation, DE) | | D | T, F (<) |
| | 38 (97) | 1342.679 | | R.NGFKSHALQLNN.R | | D | T, F (<) |
| 5 | | | EGF-like-domain, multiple 8 | | 23272552 | | |
| | 39 (98) | 958.453 | | P.E($CO_2^{1-}$)PPTSASILS | | I | F (>) |
| 6 | | | Alpha-protein kinase-3 | | 74716963 | | |
| | 40 (99) | 1052.496 | | L.ICHTGHEQAG.R | | D | T, F (<) |
| | 41 (100) | 1208.556 | | L.ICHTGHEQAGR.E | | I (m) | T |
| 7 | | | Ubiquitin hydrolase | | 1666075 | | |
| | 42 (101) | 1068.448 | | D.DDMSGDEKQ.D (2 Sodiated, DE) | | | T |
| 8 | | | Membrane-type matrix metalloproteinase | | 793763 | | |
| | 43 (102) | 1040.454 | | Y.IRE($CO_2^{1-}$)GHEKQ.A | | I | T |
| | 44 (103) | | | Y.IREGHE($CO_2^{1-}$)KQ.A | | | |
| 9 | | | DNA polymerase epsilon catalytic subunit isoform c | | 5532284 | | |
| | 45 (104) | 958.453 | | T.MAEASEDSP.R Sodiated (DE) | | D | F (>) |
| | 46 (105) | 1308.637 | | L.RSPSSLLHDPAL.H Hydroxylation (P) | | I | T |
| 10 | | | Parvin, beta | | 20127528 | | |
| | 47 (106) | 1635.891 | | S.PTPRPRRMKKDES.F Hydroxylation (P); Sodiated (DE) | | D | F (<) |

TABLE 2-continued

Plasma Peptide Biomarkers of Kidney Disease

| Protein Entry | SEQ ID NO. | Observed Mass* (m/z, z = +1) | Parent Protein | Peptide Sequence** | Gen Info. Accession (gi\|) No. | Expression RFD$ | Peptide Selection Method# |
|---|---|---|---|---|---|---|---|
| 11 | | | Complement protease C1r | | 34810714 | | |
| | 48 (107) | 972.489 | | R.VSVHPDYR.Q | | D | CA& |
| 12 | | | Hypothetical protein | | 30268186 | | |
| | 49 (108) | 1231.640 | | Y.TDSE($CO_2^{1-}$)SSASLP(OH)R.S (Sodiated, DE) | | D | F (>) |
| 13 | | | EPF autoantibody reactive epitope | | 345836 | | |
| | 50 (109) | 1738.918 | | D.RRTQEGGRGDPPPAGR.S (2 Hydroxylation, P) | | D | F (>) |
| 14 | | | C20orf42 protein | | 23273527 | | |
| | 51 (110) | 1040.454 | | V.DHPNEEQQ.K (2 Sodiated, DE) | | I | T |
| | 52 (111) | 1040.454 | | V.DHPNEEQQ.K (Gamma-carboxyl, E) | | I | T |
| 15 | | | Hypothetical protein | | 51492643 | | |
| | 53 (112) | 934.447 | | P.GLESGDIP(OH)S.P (2 Sodiated, DE) | | I | T |
| 16 | | | Unnamed protein | | 34531092 | | |
| | 54 (113) | 790.401 | | L.PHDSGQQ.H (Sodiated, DE) | | I | F (>) |
| 17 | | | MAST1 | | 38017107 | | |
| | 55 (114) | 919.476 | | S.RE($CO_2^{1-}$)TSP(OH)NR.I | | I | T |
| 18 | | | NAG-5 | | 6996651 | | |
| | 56 (115) | 1431.694 | | R.HRSHPPGWASGAR.P (Hydroxylation, P) | | D | F (<) |
| 19 | | | V-raf murine sarcoma 3611 viral oncogene homolog | | 4502193 | | |
| | 57 (116) | 1017.56 | | A.NGAE($CO_2^{1-}$)P(OH)SRAVG.T | | I | T |
| 20 | | | DEAD-box protein abstract | | 6118555 | | |
| | 58 (117) | 1842.945 | | A.RTDEVLP(OH)EEAAP(OH)RRK.M (Gamma-carboxyl, E) | | I | F (>) |
| 21 | | | PRKG1 | | 38571600 | | |
| | 59 (118) | 1762.741 | | H.YENGEYIIRQGARGD.T (Sodiated, DE) | | D | F (<) |

*Mass Accuracy ± 150 ppm
**First and last amino acids in the presented sequence are separated from the candidate peptide sequence by periods. The amino acid sequence contained within these bracketing amino acids (SEQ ID NOS: 80-118) is the proposed amino acid sequence for the candidate peptide biomarker. ( ) denotes a posttranslational modification of the preceding amino acid. ( ) at the end of a sequence indicates a modification within one or more of the amino acids listed within the parenthesis. (OH) denotes hydroxylation. (GlyGly) denotes a glycine-glycine modification to the lysine side chain epsilon amino group. ($CO_2^{1-}$) denotes gamma carboxylation of glutamic acid side chain.
The estimated statistical significance of a peptides differential expression was determined using three quantitative measures including t-test (T) at $p < 0.05$, fractional abundance (F) at fold expression increase or decrease by 1-fold, and correlation analysis (C) at greater than 0.6 correlation with a p-value less than 0.005.
C$ equals increase in peptide abundance with increased renal function decline.
C& equals increase in peptide abundance with stable renal function.
$With respect to a severe progressive increase in renal function decline, a correlative increase in plasma peptide abundance is denoted by an "I" and a correlative decrease in plasma peptide abundance is denoted by a "D". A (m) indicates a significant but marginal increased expression.

"Kidney disease", as used herein refers to an acute or chronic injury to at least one kidney of a subject, and in particular renal tubular cell injury. Kidney injury can be confirmed by any of a number of measurable criteria known in the art, including but not limited to measurement of the level of MA and renal function decline (e.g., by measuring glomerular filtration rate (GFR)) in a subject.

As used herein the expression "renal tubular cell injury" refers to a renal or kidney failure or dysfunction, either sudden (acute) or slowly declining over time (chronic). Kidney disease resulting in renal tubular cell injury can be triggered by a number of disease or disorder processes, including (but not limited to): (1) for acute renal tubular cell injury—ischemic renal injury (IRI) including acute ischemic injury and chronic ischemic injury; acute renal failure; acute nephrotoxic renal injury (NRI) toxicity including sepsis (infection), shock, trauma, kidney stones, kidney infection, drug toxicity, poisons or toxins, or after injection with an iodinated contrast dye (adverse effect); and (2) for chronic renal tubular cell injury, diabetes (T1DM or T2DM), chronic infections, chronic inflammation, glomerulonephritides, vascular diseases, interstitial nephritis, drugs, toxins, trauma, renal stones, long standing hypertension, congestive heart failure, nephropathy from sickle cell anemia and other blood dyscrasias, nephropathy related to hepatitis, HIV, parvovirus and BK virus, cystic kidney diseases, congenital malformations, obstruction, malignancy, kidney disease of indeterminate causes, lupus nephritis, membranous glomerulonephritis, membranoproliferative glomerulonephritis, focal glomerular sclerosis, minimal change disease, cryoglobulinemia, ANCA-positive vasculitis, ANCA-negative vasculitis, amyloidosis, multiple myeloma, light chain deposition disease, complications of kidney transplant, chronic rejection of a kidney transplant, chronic allograft nephropathy, and the chronic effects of immunosuppressive drugs.

Kidney disease is a common problem in many patients suffering from diabetes. In particular, diabetic nephropathy (DN) is a kidney disease that develops as a result of diabetes mellitus (DM). DM affects approximately 5% of the U.S. population, and Type 2 Diabetes Mellitus (T2DM) is the most common cause of end stage renal disease (ESRD) in the U.S. Diabetic nephropathy is believed responsible for at least 25% of all renal dialysis patients. Approximately 25% to 40% of patients with DM ultimately develop DN, which progresses through about five predictable stages, culminating in end-stage renal disease (ESRD) wherein renal replacement therapy (e.g., hemodialysis, peritoneal dialysis, or kidney transplantation) is required.

Diabetes can often result in DN and is thought to be caused by the progressive glycosylation of biomarkers, leading to a progressive loss of renal function. Diabetic nephropathy generally results in a chronic and progressive degradation of kidney function, to the point where the patient must undergo dialysis or receive a transplant to survive. Excretion of low, but abnormal, levels of albumin in the urine is considered a clinical marker of the incipient phase of nephropathy. As the glomeruli become increasingly filled with mesangial matrix products, albuminuria increases and eventually gross proteinuria appears. Microalbuminuria (MA) is defined as excretion of 30 to 300 mg of albumin per day, or an albumin-creatinine ratio between 30 and 300 in a random urine specimen. Clinical proteinuria is defined as excretion of more than 0.5 g of total biomarker a day. However, as previously discussed, MA is not a good predictor of ESRD in subjects with diabetes, because not all people who develop MA develop ESRD, and not all subjects who develop ESRD also have evidence of MA. As such, in some embodiments of the presently disclosed subject matter, the diagnostic methods disclosed herein can be used to diagnosis a diabetic subject with DN, or at risk to develop DN, even prior to presentation of clinical symptoms of DN.

The terms "polypeptide", "protein", and "peptide", which are used interchangeably herein, refer to a polymer of the 20 protein amino acids, including modified amino acids (e.g., phosphorylated, glycated, etc.) and amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein", "polypeptide" and "peptide" are used interchangeably herein when referring to a gene product and fragments thereof. Thus, exemplary polypeptides include gene products, naturally occurring proteins, homologs, orthologs, paralogs, fragments and other equivalents, variants, fragments, and analogs of the foregoing.

The terms "polypeptide fragment" or "fragment", when used in reference to a polypeptide, refers to a polypeptide in which amino acid residues are absent as compared to the full-length polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long.

A fragment can retain one or more of the biological activities of the reference polypeptide. In some embodiments, a fragment can comprise a domain or feature, and optionally additional amino acids on one or both sides of the domain or feature, which additional amino acids can number from 5, 10, 15, 20, 30, 40, 50, or up to 100 or more residues. Further, fragments can include a sub-fragment of a specific region, which sub-fragment retains a function of the region from which it is derived. When the term "peptide" is used herein, it is intended to include the full-length peptide as well as fragments of the peptide and measurable characteristics of the peptide. Thus, an identified fragment of a peptide claimed (e.g., see Tables 1 and 2 and SEQ ID NOs: 1-59) is intended to encompass the fragment, including measurable characteristics of the fragment, such as mass spectrometry observed mass, as well as the full-length peptide. In some embodiments, the kidney disease biomarker peptide can be referenced (as in Tables 1 and 2) only by a measurable characteristic (e.g., MS observed mass); however, it is intended that the full range of identifying characteristics, including peptide sequence, are intended to be encompassed by the presently-disclosed subject matter. As one example, when reference is made herein to antibodies specific for the peptides of Tables 1 or 2, it is intended that the antibodies can have specificity for the peptide fragment disclosed in the table and/or the full-length peptide.

The term "biological sample" as used herein refers to any body fluid or tissue potentially comprising one or more biomarkers associated with a kidney disease. In some embodiments, for example, the biological sample can be a saliva sample, a blood sample, a serum sample, a plasma sample, a urine sample, or sub-fractions thereof. In particular embodiments of the presently disclosed subject matter, the biological sample is a urine sample and the amounts of the one or more biomarkers determined for diagnosing a kidney disease are selected from Table 1 (e.g., SEQ ID NOS: 60-79). In other embodiments of the presently disclosed subject matter, the biological sample is a blood or plasma sample and the amounts of the one or more biomarkers determined for diagnosing a kidney disease are selected from Table 2 (e.g., SEQ ID NOS: 80-118).

The terms "diagnosing" and "diagnosis" as used herein refer to methods by which the skilled artisan can estimate and even determine whether or not a subject is suffering from a given disease or condition. The skilled artisan often makes a diagnosis on the basis of one or more diagnostic indicators, such as for example a biomarker, the amount (including presence or absence) of which is indicative of the presence, severity, or absence of the condition.

Along with diagnosis, clinical disease prognosis is also an area of great concern and interest. It is important to know the stage and rapidity of advancement of the kidney disease in order to plan the most effective therapy. If a more accurate prognosis can be made, appropriate therapy, and in some instances less severe therapy for the patient can be chosen.

Measurement of biomarker levels disclosed herein (e.g., Tables 1 and 2) can be useful in order to categorize subjects according to advancement of kidney disease who will benefit from particular therapies and differentiate from other subjects where alternative or additional therapies can be more appropriate.

As such, "making a diagnosis" or "diagnosing", as used herein, is further inclusive of determining a prognosis, which can provide for predicting a clinical outcome (with or without medical treatment), selecting an appropriate treatment (or whether treatment would be effective), or monitoring a current treatment and potentially changing the treatment, based on the measure of diagnostic biomarker levels disclosed herein.

The phrase "determining a prognosis" as used herein refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the presence, absence or levels of test biomarkers. Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., not expressing the biomarker or expressing it at a reduced level), the chance of a given outcome may be about 3%. In certain embodiments, a prognosis is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance.

The skilled artisan will understand that associating a prognostic indicator with a predisposition to an adverse outcome is a statistical analysis. For example, a biomarker level (e.g., quantity of expression in a sample) of greater than a control level in some embodiments can signal that a subject is more likely to suffer from a kidney disease than subjects with a level less than or equal to the control level, as determined by a level of statistical significance. Additionally, a change in marker concentration from baseline levels can be reflective of subject prognosis, and the degree of change in marker level can be related to the severity of adverse events. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In other embodiments, a threshold degree of change in the level of a prognostic or diagnostic biomarker can be established, and the degree of change in the level of the indicator in a biological sample can simply be compared to the threshold degree of change in the level. A preferred threshold change in the level for markers of the presently disclosed subject matter is about 5%, about 10%, about 15%, about 20%, about 25%, about 30%, about 50%, about 75%, about 100%, and about 150%. In yet other embodiments, a "nomogram" can be established, by which a level of a prognostic or diagnostic indicator can be directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments of the presently disclosed subject matter, multiple determination of one or more diagnostic or prognostic peptide biomarkers can be made, and a temporal change in the biomarker can be used to monitor the progression of disease and/or efficacy of appropriate therapies directed against the disease. In such an embodiment for example, one might expect to see a decrease or an increase in the biomarker(s) over time during the course of effective therapy. Thus, the presently disclosed subject matter provides in some embodiments a method for determining treatment efficacy and/or progression of a kidney disease in a subject. In some embodiments, the method comprises determining an amount of at least one peptide biomarker associated with kidney disease, such as for example at least one peptide of Table 1 (e.g., SEQ ID NOS: 60-79), Table 2 (e.g., SEQ ID NOS: 80-118), or both, in biological samples collected from the subject at a plurality of different time points and comparing the amounts of the at least one peptide in the samples collected at different time points. For example, a first time point can be selected prior to initiation of a treatment and a second time point can be selected at some time after initiation of the treatment. One or more biomarker levels can be measured in each of the samples taken from different time points and qualitative and/or quantitative differences noted. A change in the amounts of the biomarker levels from the first and second samples can be correlated with determining treatment efficacy and/or progression of the disease in the subject.

The terms "correlated" and "correlating," as used herein in reference to the use of diagnostic and prognostic biomarkers, refers to comparing the presence or quantity of the biomarker in a subject to its presence or quantity in subjects known to suffer from, or known to be at risk of, a given condition (e.g., a kidney disease); or in subjects known to be free of a given condition, i.e. "normal individuals". For example, a biomarker level in a biological sample can be compared to a level known to be associated with a specific type of kidney disease. The sample's biomarker level is said to have been correlated with a diagnosis; that is, the skilled artisan can use the biomarker level to determine whether the subject suffers from a specific type of kidney disease, and respond accordingly. Alternatively, the sample's biomarker level can be compared to a control marker level known to be associated with a good outcome (e.g., the absence of kidney disease), such as an average level found in a population of normal subjects.

In certain embodiments, a diagnostic or prognostic biomarker is correlated to a condition or disease by merely its presence or absence. In other embodiments, a threshold level of a diagnostic or prognostic biomarker can be established, and the level of the indicator in a subject sample can simply be compared to the threshold level.

As noted, in some embodiments, multiple determination of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type of kidney disease, or a given prognosis. Likewise, a decrease in the marker from the initial time to the second time can be indicative of a particular type of kidney disease, or a given prognosis. Furthermore, the degree of change of one or more markers can be related to the severity of kidney disease and potential for future adverse events.

The skilled artisan will understand that, while in certain embodiments comparative measurements can be made of the same diagnostic marker at multiple time points, one can also measure a given marker at one time point, and a second marker at a second time point, and a comparison of these markers can provide diagnostic information.

Numerous methods and devices are well known to the skilled artisan for the detection and analysis of the biomarker peptides of the presently disclosed subject matter. With regard to polypeptides or proteins in subject test samples, mass spectrometry and/or immunoassay devices and methods can be used, although other methods are well known to those skilled in the art (for example, the measurement of marker RNA levels). See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

In certain embodiments of the presently disclosed subject matter, the biomarker peptides are analyzed using an immunoassay. The presence or amount of a peptide marker can be determined using antibodies or fragments thereof specific for each peptide marker and detecting specific binding. For example, in some embodiments, the antibody specifically binds a peptide of Table 1 (e.g., SEQ ID NOS: 60-79) or Table 2 (e.g., SEQ ID NOS: 80-118), which is inclusive of, but not limited to, antibodies that bind the full-length peptide as well. In some embodiments, the antibody is a monoclonal antibody.

Any suitable immunoassay can be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies or fragments thereof specific for the markers is also contemplated by the present subject matter. The antibodies can be immobilized onto a variety of solid substrates, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on solid support. This strip can then be dipped into the test biological sample and then processed quickly through washes and detection steps to generate a measurable signal, such as for example a colored spot.

In some embodiments, a kit for the analysis of biomarkers is provided that comprises antibodies having specificity for one or more biomarkers associated with kidney disease. The antibodies can be bound to a substrate, as disclosed herein. Such a kit can comprise devices and reagents for the analysis of at least one test sample. The kit can further comprise instructions for using the kit and conducting the analysis. Optionally the kits can contain one or more reagents or devices for converting a marker level to a diagnosis or prognosis of the subject.

In some embodiments, mass spectrometry (MS) analysis can be used alone or in combination with other methods (e.g., immunoassays) to determine the presence and/or quantity of the one or more biomarkers of interest in a biological sample. In some embodiments, the MS analysis comprises matrix-assisted laser desorption/ionization (MALDI) time-of-flight (TOF) MS analysis, such as for example direct-spot MALDI-TOF or liquid chromatography MALDI-TOF mass spectrometry analysis. In some embodiments, the MS analysis comprises electrospray ionization (ESI) MS, such as for example liquid chromatography (LC) ESI-MS. Mass analysis can be accomplished using commercially-available spectrometers, such as for example triple quadrupole mass spectrometers. Methods for utilizing MS analysis, including MALDI-TOF MS and ESI-MS, to detect the presence and quantity of biomarker peptides in biological samples are known in the art. See for example U.S. Pat. Nos. 6,925,389; 6,989,100; and 6,890,763 for further guidance, each of which is incorporated by reference herein in its entirety. In some embodiments, the MS analysis can be utilized to identify specific polypeptide sequences and corresponding proteins and amounts compared to controls to diagnose a kidney disease. However, MS analysis can also be utilized with the methods of the presently-disclosed subject matter to determine a measurable characteristic of the peptide biomarkers, and in particular a MS observed mass. As such, "determining an amount" of one or more peptides of Tables 1 and 2 by MS analysis is inclusive of determining amounts of full-length polypeptides inferred from peptide fragment analysis by MS, specifically-identified peptide (e.g., polypeptide sequences set forth in SEQ ID NOs: 1-59) fragment amounts, as well as MS observed mass peak analysis.

The analysis of a plurality of markers can be carried out separately or simultaneously with one test sample. Several markers can be combined into one test for efficient processing of a multiple of samples. In addition, one skilled in the art would recognize the value of testing multiple samples (for example, at successive time points) from the same subject. Such testing of serial samples will allow the identification of changes in biomarker levels over time. Increases or decreases in marker levels, as well as the absence of change in marker levels, can provide useful information about the disease status that includes, but is not limited to identifying the approximate time from onset of the disease, the presence and amount of functioning tissue, the appropriateness of drug therapies, the effectiveness of various therapies, differentiation of the various types and stages of kidney diseases, identification of the severity of the disease, and identification of the subject's outcome (prognosis), including risk of future events.

A panel consisting of biomarkers associated with a kidney disease (e.g., the biomarker peptides of Tables 1 and/or 2) can be constructed to provide relevant information related to the diagnosis or prognosis of the kidney disease and management of subjects with the kidney disease. Such a panel can be constructed, for example, using 1, 2, 3, 4, 5, 6, 7, 8, 9, 10, 15 or 20 individual biomarkers. The analysis of a single marker or subsets of markers comprising a larger panel of markers can be carried out by one skilled in the art to optimize clinical sensitivity or specificity in various clinical settings. These include, but are not limited to ambulatory, urgent care, critical care, intensive care, monitoring unit, in-patient, out-patient, physician office, medical clinic, and health screening settings. Furthermore, one skilled in the art can use a single marker or a subset of markers comprising a larger panel of markers in combination with an adjustment of the diagnostic threshold in each of the aforementioned settings to optimize clinical sensitivity and specificity. The clinical sensitivity of an assay is defined as the percentage of those with the disease that the assay correctly predicts, and the specificity of an assay is defined as the percentage of those without the disease that the assay correctly predicts (Tietz Textbook of Clinical Chemistry, 2.sup.nd edition, Carl Burtis and Edward Ashwood eds., W.B. Saunders and Company, p. 496).

The analysis of markers can be carried out in a variety of physical formats as well. For example, the use of microtiter plates or automation could be used to facilitate the processing of large numbers of test samples. Alternatively, single sample formats can be developed to facilitate immediate treatment and diagnosis in a timely fashion, for example, in ambulatory transport or emergency room settings.

Further with respect to the methods of the presently disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently disclosed subject matter.

As such, the presently disclosed subject matter provides for the treatment and testing of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the testing and treatment of livestock, including, but not limited to, domesticated swine, ruminants, ungulates, horses (including race horses), poultry, and the like.

In some embodiments, the subject tested is afflicted with or was previously afflicted with a disease other than kidney disease. In particular, the other disease can be a disease linked to or predisposing one to kidney disease. For example, in some embodiments, the subject is a diabetic subject, as diabetes can be a risk factor for developing kidney disease. In some embodiments, the subject is a diabetic subject suffering from, or at risk of suffering from, diabetic nephropathy.

The practice of the presently disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

We have identified several peptides from a number of unique gene products (see Table 1) that are present in the urine and are discriminatory markers of renal function decline (RFD) in Type 1 diabetes (TI DM) patients with microalbuminuria (MA). Three novel approaches were employed to identify the biomarkers: patient sample selection; peptide extraction; and analysis.

Sample Selection—The urine samples we studied to identify biomarkers of diabetic RFD were obtained from T1DM patients. The samples we studied were collected from a time (n=62) point preceding any loss of GFR. Samples used were developed from the $1^{st}$ Joslin Cohort of the NIH funded project titled "Natural History Study of Microalbuminuria in Type 1 Diabetes (R01 DK41526). A cohort of 1394 T1DM individuals was followed for >8-10 years. Patient samples used to generate our preliminary data presented with confirmed MA (albumin excretion rate (AER) of 30-300 μg/min) during the two years preceding urine collection. Patients with non-diabetic kidney disease were excluded. The urine samples were matched between groups for age (54.5 yr±5 yr), gender and glycemic control (Hb Alc levels). Case samples (n=19) encompassed individuals with significant early progressive renal function decline. These individuals experienced an annual loss of more than 3.4 mL/yr in their estimated glomerular filtration rate (eGFR) as measured by serum cystatin C. Control samples (n=42) encompassed individuals with renal function decline that was approximately equal to the loss experienced as a result of the normal aging process. These individuals experienced an annual loss of less than 3.4 mL/yr in their estimated glomerular filtration rate (eGFR) as measured by serum cystatin C. The samples analyzed to generate the presently disclosed biomarkers were developed from banked patient urine samples collected before any of the patients experienced RFD. Thus, observed differences in the urine peptidome can reflect or correlate with the future development of RFD.

Peptide Extraction—The method used to extract urine peptides for biomarker studies is one developed and optimized by our group over the last three years. Briefly, peptides were isolated from urine in a two-step process. The urine peptides were first size selected from the proteins by ultrafiltration that produced a low molecular weight peptide panel having a mass less than 10,000 Daltons. We have determined from several hundred analyses that as little as 1 mL urine provides >500 μg urinary peptide (as 82 BCA peptide assay positive material).

A single capillary HPLC analysis requires 1-5 µg peptide and hence enough peptide material for the proposed project from a single mL of urine. The peptides were then concentrated, desalted, and mass quantified.

Data Acquisition and Analysis—Equivalent masses of peptides were separated by 1D-RP-capillary HPLC and analyzed using high-sensitivity, high-throughput MALDI-TOF MS. A challenge in using MS analysis of clinical samples is the remarkable dimensionality of the spectra data sets. Our data analysis approach is to apply both supervised and unsupervised informatic methods. In our approach, statistical analysis of urinary peptide profiles using LC-MALDI peak lists began with unsupervised sorting of the MS data using Principle Components Analysis (PCA) or Hierarchical Clustering (HC) followed by group annotation. This approach is more robust and has less intrinsic bias. In some cases, supervised sorting of the sample MS data was required. In those cases the investigator assigned the MS spectral data into groups. Principle data sets were developed from MALDI-TOF spectral files. Here, the data were extracted from MALDI-TOF spectral files (.t2d files) using instrument manufacturer software (PEAK EXPLORER) and these peak lists were imported into analytical/statistical software for analysis. One software package (MARKERVIEW™) imports the peak list data as .txt files. Peak list data contains information for peptide retention time, m/z, and signal response. These data were then imported with use of filters to remove masses associated with internal standards and matrix contaminants, adjustment of retention times and for mass accuracy. In either case of group membership assigned by unsupervised or supervised methods, MS spectral data were compared by univariate (student's t-test or Mann-Whitney t-test constrained by false discovery rate analysis, FDR) or multivariate methods (PCA; RandomForest, RE, or receiver operator characteristic (ROC) curves). With these approaches we were able to simultaneously analyze thousands of features. To correct for simultaneous multiple hypothesis testing we estimated the q-value for every feature in order to estimate the FDR. We assumed a false discovery rate of 0.10 was acceptable and hence any feature with a q-value less than 0.10 was considered significant. Peptide masses having sufficient specificity to sort MALDI-TOF MS spectra into groups were tabulated and selected for MALDI-TOF MS/MS analysis Prior to PCA analysis by MARKERVIEW™, data were imported, preprocessed using logarithmic data weighting and automatic data scaling filters. Patient urinary peptide samples were assigned to Groups and the imported/preprocessed data compared by two univariate statistical methods (unpaired, two-tailed students t-test and Mann-Whitney test) to discern peptides that were presented at levels significantly different between Groups. Only patient samples representing the extremes of eventual RFD or stability were initially selected for analysis (n=15). Unsupervised PCA demonstrates that dominate differences in the patients urinary peptide profiles sort the samples into two clear groups.

In addition to PCA analysis, an expanded sample set (n=49) of individuals with low to moderate RFD ($\leq$-3.5 mL/yr) and moderate to high RFD ($\geq$-3.5 mL/yr) were used for unsupervised sorting analysis. Here the LC-MALDI TOF MS peak list data were classified with their urinary polypeptide profiles using HC classification algorithms with subsequent selection of classifying peptides by RF and ROC analyses. We calculated the most important features determined by the RF algorithm in terms of Gini index and mean square error. In order to minimize the effect of stochastic nature of the RF procedure we ran the algorithm a large number of times (>100) and determined the most important common features amongst all the runs. RF was utilized for selection of variables with two measures of variable importance utilized: 1) average decrease in classification accuracy and 2) Gini importance (average decrease of Gini index). RF parameters were estimated by minimizing generalization error estimate and maximizing stability of variable ranking, computed as the cardinality of intersection of the 20 top ranked features over 100 RF runs. After each run variables with corresponding importance measures smaller or equal to 0 were discarded. Following supervised and unsupervised comparison, we have identified upwards of 40 peptides that were associated with RFD in diabetics.

Additional Data Acquisition and Analysis:

Analysis of MALDI-TOF MS Data Sets—The statistical analysis of the data was broken down into three types of analysis: class discovery, class prediction, and class differentiation methods. With all methods the MS data sets were developed using aligned LC-MALDI-TOF MS peptide peak lists with the peptide data arrayed as mass (m/z; +1) and retention time pairs. Peptide abundance was assigned based on the peptide MALDI-TOF MS ion cluster area.

Class discovery methods—The class discovery methods used primarily involved several types of cluster analysis. Initially Principal Components Analysis (PCA) and hierarchical cluster analysis using a variety of weight (correlation, Euclidian) and link functions (average, single, complete) was conducted. In addition the non-hierarchical cluster K-means clusters was used on the data. We used s/n 3 and s/n 10 data, with and without natural log. PCA is a graphical method to illustrate similarities of different samples within groups based on sample characteristics such as peptide abundance in the present study. A PCA plot illustrates the relationship of sample or sample data based on the two dominate sets of sample variance. Therefore a PCA plot is a qualitative tool to define sample groups in an unbiased fashion. Classical parametric and non-parametric tests can then be used to identify the specific differences between the groups.

Class differentiation methods—To determine differences in peak intensity between the cases and controls we used a t-test and adjusted the p-values using a Benjamini and Hochberg False Discover Rate procedure. We addressed the problem by holding RFD as a "continuum" of pathophysiology and analyzed the entire MS data set. The slope of the decline in renal function and well as covariate data was regressed on the peak intensities (s/n3, s/n10, with and without natural log scaling) and significance was assessed using simple linear regression and correlations with Pearson's correlation. This has the effect of assigning no specific rate of RFD to distinguish decliners from non-decliners. The data were then analyzed for correlation of peptide abundance with RFD (slope glm) using Spearman correlations calculations for the intensity of peptide mass-retention time pairs and slope glm. Peptide mass-rt pairs with Spearman correlation values >0.3 and <-0.3 then filtered by parametric t-tests. The Spearman correlation coefficients values were filtered using minimum correlation cutoff values of less than or equal to −0.3 or greater than or equal to +0.3 and then by a second t-test filter. All peptides having a minimum Spearman correlation coefficient value and parametric t-tests with a p-value less than 0.01 were considered as significant. The FDR that was returned for these computations ranged from 0.35 to 0.89. Peptides having parametric t-tests p<0.01 were accepted as significant (Table 1). The MALDI-TOF MS spectra for these masses were then visually reviewed for further MS/MS analyses. In separate analyses, we computed the fractional peptide-presence/absence to remove the quantification error resulting from variability in observed MALDI-TOF MS signal intensity. The data were analyzed by a clinical definition of RFD and by designation of phenotypic extremes (tertile extremes). First, the samples were designated as RFD (+) and RFD (−) based on the rate of RFD in a normal population (−3.3 slope glm). Observed peptide masses were assigned an intensity of "1" and unobserved masses assigned an intensity of "0". The fractional presence of each peptide was computed for case (decliner) and control (non-decliner) samples. The fractional abundance (f) of each case and control peptide was used to compute a fractional abundance ratio ($f_{case}/f_{control}$). Fractional abundance ratio's greater than 2 or less than 0.5 in the tertile population were considered significantly differentially expressed within the RFD populations. Next the ratio of fractional presentation of case (decliner)/control (non-decliner) was computed to determine the relative expressional abundance of a peptide within the sample population.

Class prediction (discriminate) analysis—Using the unselected s/n 3 and s/n 10 data separately, we conducted discriminate analysis using a grid of significance levels (0.01, 0.05, 0.2) on the decliner verses non-decliner patients. We evaluated a number of multivariate classification methods, including the Compound Covariate Predictor, Diagonal Linear Discriminant Analysis, Nearest Neighbor Predictor, Nearest Centroid Predictor, and Support Vector Machine Predictor. We used leave-one-out cross validation to generate the final models as well as to determine the accuracy of the models. Sensitivity, specificity, Positive and Negative predictive values for each of the models was obtained.

Examples 2-9

We hypothesized that qualitative differences in urine proteins might provide insight into the etiology of progressive ERFD and serve as putative biomarkers of risk of progressive ERFD. To address this hypothesis, in these examples we have performed proteomic and peptidomic analyses of urine samples obtained during the Joslin Study of the Natural History of Microalbuminuria in Type 1 Diabetes. In the present examples, the low molecular weight protein (<10 kDa), or peptidomic, fraction in urine was analyzed. We compared urine peptide expression in patients with MA who retained stable renal function to those with MA and EFRD. Our data demonstrate that the urinary expression of several protein fragments differs significantly between microalbuminuric diabetic patients who develop ERFRD compared to microalbuminuric diabetic patients who do not develop ERFD. Two such peptides, fragments of inositol pentakisphosphate 2-kinase (IPP2K) and zona occludens-3 (ZO-3) were further studied in human renal biopsies to determine if urine peptide fragments correlate with renal protein expression. In biopsies from T1D patients with early signs of diabetic nephropathy, ZO-3 expression in renal tubular epithelial cells was increased compared to controls and ZO-3 translocated to the cytoplasm. IPP2K expression was increased and co-localized in renal tubules with granule-like cytoplasmic structures. T-cell intracellular antigen-1 related protein (TIAR), a protein associated with stress granules, was also increased in diabetic kidney biopsies. These results confirm that urine peptide analysis can define pathogenic mechanisms of kidney disease including diabetic nephropathy and that the urine peptidome contains biomarkers that correlate with the future development of diabetic renal disease.

Methods for Example 2-9

Patient Selection and Case Definition for Early Renal Function Decline (ERFD). The protocol and consent procedures were approved by the Committee on Human Studies of the Joslin Diabetes Center and the University of Louisville. Among the 943 patients with normoalbuminuria enrolled in the 1$^{st}$ Joslin Study of the Natural History of Microalbuminuria in Type 1 Diabetes, MA developed in 109 during the first four years of follow-up[2], it is this cohort of 109 patients with a documented onset of MA that is the population potentially eligible for this study.

Diagnoses of normoalbuminuria and microalbumuria were based on multiple measurements of the albumin excretion rate (in micrograms per minute), which was estimated from the albumin-to-creatinine ratio in random urine samples as previously described. (1, 2) Eighty six patients were followed until 2007, and 61 met the following additional criteria for inclusion in the analysis: 1) follow-up examinations spanning at least 8 years after the onset of MA for the estimation of the slope of GFR over time; 2) at least one 6 ml aliquot of stored urine from an examination within five years of the onset of MA for analysis of peptide components. Among available urine samples, the earliest after MA onset was selected.

The 61 patients were divided into cases of ERFD and controls according to the regression slope fitted to their follow-up estimates of GFR based on serum cystatin C (cC-GFR). The protocol used for assessment of early progressive renal function decline has been described in detail previously. (8, 17) In brief, glomerular filtration rate in ml/min was approximated numerically by the reciprocal of cystatin C (in mg/L) multiplied by 100. A regression slope fitted to serial measurements of cC-GFR over eight years accurately tracks the trend in renal function over that time. Patients had, on average, 4.8 cC-GFR estimates. As previously published, we used the longitudinal data available from the Baltimore Aging Study as the reference distribution for evaluating whether a negative slope or trend in renal function qualified as an abnormal rate of decline (designated 'early renal function decline' or 'ERFD'). (7)

Sample Handling and Peptide Isolation. The order of case or control sample handling during peptide isolation was randomized to minimize technical or methodological bias during data collection. Urinary peptides were isolated from the urine less than 10 kDa ultrafiltrate by solid phase extraction (SPE) methods, filtered through regenerated cellulose syringe filter (0.2 μm National Scientific Co.), and transferred to autosampler vials in a final concentration of 0.1 μg/μL. Peptides (5 μg) were separated using a reversed-phase capillary scale column (Dionex 75 μm I.D. Nano Series Column, C18 PepMap 100, 3 μm, 100 Å) with 45 min Solvent A (0.05% trifluoroacetic acid (TFA) to Solvent B (80% acetonitrile (ACN)/0.05% TFA) gradient and 45 1-min fractions were collected with a robotic fraction collector (Accuspot, Shimadzu Corp., Kyoto, Japan). MALDI matrix (5 mg/mL α-CN (α-Cyano-4-hydroxycinnamic acid) and a 5.33 fmol/μL angiotensin I (AT I) standard dissolved in 50% ACN/0.1% TFA) was overlaid onto dried LC fractions collected on archivable MALDI sample plates (ABI Opti-TOF plates) post run using the Accuspot to include an internal mass calibration standard at 4 fmol AT-I per spot.

Positive ion MALDI—TOF mass spectra were acquired using an Applied Biosystems (Foster City, Calif.) AB4700 Proteomics Analyzer operating in reflectron mode and with ion source pressure ~0.5 μTorr. After a 400 ns time-delayed ion extraction period, the ions were accelerated to 20 kV for TOF mass spectrometric analysis. A total of 1000 laser shots (355 nm Nd:YAG solid state laser operating at 200 Hz) were acquired and signal averaged. MALDI-TOF spectra were exported as .t2d files as well as peak list files for chromatographic data alignment and for analysis by MarkerView (MDS Sciex).

Analysis of MALDI-TOF MS Data Sets. Aligned MS data sets were constructed (peptide mass (m/z; +1) and retention time pairs) with peptide abundance based on the MS ion cluster area. The prevalence of peptide abundance was determined. Cases of early renal function decline were defined by loss in GFR that exceeded −3.3%/yr, a threshold that corresponds to the 2.5th percentile of the distribution of GFR slopes in an independent non-diabetic normotensive population. Observed peptide masses were assigned an intensity of "1" and unobserved masses assigned an intensity of "0". The fractional abundance (f) of each case and control peptide was used to compute a fractional abundance ratio ($f_{case}/f_{control}$). Fractional abundance ratio's greater than 1.5 or less than 0.5 in case-to-control ratios were considered significantly differentially expressed within the two populations. The fractional abundance ratios for these peptides were reconsidered using only the patient samples found in the first and third tertile. Peptides having a ratio that became more extreme (greater than 1.5 or less than 0.5) were tabulated for further MS/MS analyses. To determine the correlation of peptide expression with ERFD, the slope of the decline in renal function (slope glm) was regressed on the s/n 3 peak intensities with natural log scaling and significance was assessed using simple linear regression and correlations with Spearman rank order correlation analysis for the tertile extremes. The Spearman correlation coefficients values were filtered using minimum correlation cutoff values of less than or equal to −0.4 or greater than or equal to +0.4. The goodness of the correlation fit was determined by a t-test filter. All peptides having a minimum Spearman correlation coefficient value and parametric t-tests with a p-value less than 0.01 were considered as significant. Peptides having parametric t-tests p<0.01 were accepted as significant (Table 1) were tabulated for further MS/MS analyses.

Peptide Sequence Tagging of Selected Peptide Ions using MALDI-TOF/TOF MS. Fragmentation data, post-source-decay (PSD) and collision-induced-dissociation (CID) data, were collected for each tabulated peptide using the AB4700 MALDI TOF/TOF using 1 KeV collision energy, atmospheric gases (medium pressure) and collection averaged data from 1500 laser shots.

Concatenated lists of averaged fragmentation spectra (PSD and CID) were submitted for computer assisted data analysis. Analyses were conducted in an iterative fashion with the concatenated lists starting with search parameters of a mass accuracy of 0.15 Da for peptides and 0.3 Da for fragment masses. Sequence tagging analyses of MALDI TOF/TOF spectra were achieved using a combination of Global Protein Server (GPS) software (Applied Biosystems, Foster City, Calif.) and Matrix Science Mascot version 2.1 with manual review of all returned analyses. Peptide fragmentation peak lists were searched against the unconstrained (non enzyme) NCBInr 20060712 database (3783042 sequences, 1304471729 residues) with *Homo sapiens* taxonomy (111934 sequences) initially with no PTM's and proceeding sequentially with addition of possible PTM's sodiation and hydroxylation. Mascot search of the MALDI TOF-TOF data proceeded with assuming possible hydroxylation of lysine (K), asparagine (N), proline (P), and possible sodiation of aspartic acid (D) or glutamic acid (E) side chains or carboxy termini. Returned Mascot probabilistic scores for peptides of ≧67 indicate identity or extensive homology (p<0.05). As Mascot scoring is biased against single peptide identification, manual review of returned MASCOT fragmentation data analyses was conducted and used to make sequence tagging assignments. Data were then re-searched using a NCBInr *Homo sapiens* decoy database constructed using the online tool from Matrix Science MASCOT for randomization of database protein sequences. The top peptide assignments by the *Homo sapiens* and the *Homo sapiens*-decoy databases were rank ordered and masses having a higher *Homo sapiens*-decoy rank order were discarded and not used for further analyses. Fragmentation spectra assigned a MASCOT scores of ≧20 for m/z<3,000 and of ≧10 for m/z>3,000 were manually reviewed using acceptance criterion including y-, b-, a-, ya- and yb-ion coverage, percentage of fragmentation spectra assigned, root mean square (rms) mass accuracy errors for precursor (rms<50 ppm) and precursor fragmentation products (rms<500 ppm).

Immunohistochemistry (IHC). A modified version of a previously described IHC protocol was used. Formalin fixed, paraffin embedded kidney sections from human biopsy specimens were obtained and sections were dewaxed, treated with antigen unmasking solution (H-3300 from Vector Laboratories Inc, Burlingame Calif.), and endogenous peroxidase activity was blocked. Kidney sections were selected from three different normal, disease control and disease biopsy specimens. Kidney sections were blocked, probed with primary antibody (1:1,000 dilution mouse polyclonal antibody to IPP2K; cat. no. H00064768-A01, Novus Biologicals Inc, Littleton, Colo.), probed with secondary antibody and treated with ABC reagent. For negative controls, serial sections were stained as before with the exception of no primary antibody. Processed sections were scored by three blinded individuals using a scoring rubric for staining to nuclei, cytoplasm, basement membrane, and interstitium. Negative control and deletion control experiments were conducted to optimize for antibody combination, antibody concentration, incubation times, and order of antibody visualization.

Example 2

Characteristics of the Study Population

The study population was comprised of the patients whose onset of microalbuminuria (MA) was documented in the 1st Joslin Study of the Natural History of Microalbuminuria in Type 1 Diabetes. Additional eligibility criteria included follow-up examinations spanning at least 8 years after MA onset for estimating the rate of GFR decline and availability of a 6 ml aliquot of stored urine for peptide analysis. The 61 patients who met all eligibility criteria were subdivided into 19 cases with early renal function decline, defined as a decline of 3.3% or more per year (range: −3.3 to −16.1% per year), and 42 controls with lesser rates of renal function decline (range: +1.9 to −3.2% per year). For illustration, contrasting examples of longitudinal changes in renal function are shown in FIG. 1. Both patients had T1D and MA. The control patient experienced age-appropriate renal function decline (approximately 1% per year), while the case patient with ERFD progressed to end-stage renal disease.

Characteristics of the case and control groups are summarized in Table 3 at the onset of MA (Section A) and at the examination (approximately 3 years later) that provided the urine sample for peptide analysis (Section B). All patients were Caucasian and the groups had similar distributions of sex and duration of diabetes at the onset of MA. ERFD cases were older and had higher average glycated hemoglobin A1c than controls, but had the same estimated GFR (cC-GFR) (Table 3, section A). At the time of urine sampling for peptide analysis (Table 3, Section B) the groups had similar MA duration, blood pressure, urinary albumin excretion and medications. Glycated hemoglobin continued to be higher in cases than controls. The cC-GFR had declined slightly in both cases and controls from the time of MA onset, but still remained in the normal range. The cC-GFR was not below 60 ml/min in any patient during these baseline intervals. At the end of follow-up (Table 3, Section C), the mean duration of follow-up from the onset of MA for both cases and controls was approximately 12 years (about 10 years after the time when urine samples were obtained for this study). By design, the rate of renal function loss (cC-GFR slope) was much greater in cases of ERFD (−6.5% per year mean change) than in controls (−1.4% per year mean change). As a result of this disparity in renal function deterioration, advanced chronic kidney disease or end-stage renal disease developed in half of the cases.

TABLE 3

Characteristics of Patients at Three Points in Time (Onset Microalbuminuria, Collection of Urine Sample, and End of Follow-up) According to Whether Early Renal Function Decline (ERFD) Developed During Follow-up

| Characteristics: | ERFD - Yes Cases n = 19 | ERFD - No Controls n = 42 |
|---|---|---|
| A. Onset of microalbuminuria | | |
| Duration of DM (y) 0.23 | 20 ± 8.5 | 18 ± 8.2 |
| Age (y) 0.02 | 36 ± 7.7 | 31 ± 7.5 |
| HbA1c (%) 0.03 | 9.5 ± 1.4 | 8.7 ± 1.3 |
| cC-GFR ml/min 0.89 | 148 ± 25 | 149 ± 24 |
| B. Collection of urine sample for peptide analysis | | |
| Duration of microalbuminuria (y) 0.22 | 2.7 ± 1.5 | 3.2 ± 1.5 |
| HbA1c (%) 0.004 | 9.7 ± 1.5 | 8.4 ± 1.5 |
| Systolic blood pressure 0.20 | 127 ± 21 | 121 ± 14 |
| Urinary albumin excretion (µg/min) 0.33 | 39.8 (14.5, 53.1) | 25.4 (10.2, 39.0) |
| Use of ACE inhibitors (%) 0.10 | 74 | 51 |
| cC-GFR ml/min 0.14 | 128 ± 27 | 138 ± 25 |
| C. End of follow-up | | |
| Duration of follow-up (y)* 0.37 | 11.6 ± 1.3 | 12.0 ± 2.1 |
| cC-GFR slope (%/y) <0.001 | −6.5 ± 3.5 | −1.4 ± 1.2 |
| Urinary albumin excretion (µg/min) | 1200 (300, 3000) | 75 (5, 750) |
| Chronic Kidney Disease Stage ≧3 (%) | 58† | 0 |

Data are mean ± SD except for urinary albumin excretion which is median (25$^{th}$, 75$^{th}$ percentile) and categorical variables which are percents.
*Time interval between the onset of microalbuminuria and the last determination of cc-GFR.
†During follow-up, Stage 3 chronic kidney disease developed in 11 cases and end-stage renal disease developed in 3 of the 11.
DM, diabetes mellitus; HbA1c, hemoglobin A1c; ACE, angiotensin converting enzyme Example 3

Urine Peptide Analysis

Statistical analysis of the LC-MALDI-TOF MS data sets presented several challenges. First, only a few individual peptides were observed in every sample. For example, while 5,297 different peptides were observed, only 1,206 peptides were present in 50% of samples. The large numbers of undetected peptides introduced an equivalently large number of null values into the data sets; thus discouraging the application of classical t-test methods to select for differentially expressed peptides.

In order to focus effort on the most promising peptides, we imposed three stringent criteria for selecting peptides for further analysis. First, we eliminated the 3,364 peptides that were detected in less than 25% of the samples. Second, we required that there be a 50% difference in the detection frequency of a peptide between cases and controls. This reduced the number of peptides to 12. Third, we added a quantitative requirement to the evidence for association. Peptide quantity was calculated from its peak characteristics using integrated signal intensity. We then calculated the Spearman correlation coefficient between the peptide abundance and the rate of renal function loss, and selected four peptides with strong correlation (Table 4) for further analysis in these examples. All four had coefficients less than −0.40 and a p-value less than 0.01

TABLE 4

Urinary Peptides Determined To Be Differentially Present Between Case And Control Samples

| | Proportion (%) of Urine Samples with Detectable Peptide | | | | | Proportion (%) of Urine Samples with Detectable Peptide | | |
|---|---|---|---|---|---|---|---|---|
| Peptide Mass (m/z) | Cases N = 19 | All Controls N = 42 | Ratio | Correlation with GFR Slope | P-value | Cases N = 19 | Super Controls N = 20 | Ratio |
| 842.347 | 79 | 43 | 1.8 | −0.405 | 0.001 | 79 | 40 | 1.9 |
| 983.535 | 42 | 19 | 2.2 | −0.437 | 0.006 | 42 | 5 | 8.4 |
| 1190.633 | 42 | 17 | 2.5 | −0.416 | 0.001 | 42 | 10 | 4.2 |
| 1838.851 | 63 | 33 | 1.9 | −0.421 | 0.008 | 63 | 20 | 3.2 |

Example 4

Determination if Urine Peptides that Identify Patients with Renal Function Decline were Present in Contemporaneous Plasma Samples The discriminating peptides present in urine had a molecular weight (m/z) ranging approximately from 842 to 1838 Da and therefore might be present in the urine after being freely filtered from the plasma by the glomerulus. To investigate the source of the selected peptides, we conducted additional LC-MALDI-TOF MS experiments of plasma samples obtained with the urine samples we had analyzed. We performed LC-MALDI TOF MS analysis of plasma peptides isolated from samples collected from the same individuals supplying the urine samples used in this study. The samples were available from 18 case and 18 control patients. The isolated serum peptides were analyzed using identical LC-MALDI TOF MS methods employing chromatography retention time internal standards and on-plate per spot internal mass calibration standards.

One plasma peptide was detected in a majority of plasma samples at the correct chromatographic retention time and with the correct mass (1190.638 m/z±150 ppm mass accuracy) to be assigned to one of the four urinary peptides which correlating with ERFD and which were further analyzed in the present examples. However there was no difference in this peptide's plasma abundance between Case and Control patients.

Example 5

Identification of RFD Discriminating Urine Peptide Amino Acid Sequence by Mass Spectrometry To better understand ERFD mechanisms we sought to identify the protein source for the discriminating urinary peptides selected for further analysis in these examples. We performed tandem mass spectrometry analysis to identify the amino acid sequence of the discriminating urine peptides.

As seen in Table 5, a total of three peptide sequence identifications were made including fragments of the cadherin-like protein FAT tumor suppressor 2, ZO-3 and a fragment of IPP2K. Further MS analysis demonstrated that the 1838.782 m/z ion had a peptide sequence having a missed trypsin cleavage site due to the presence of a glycyl-glycyl post-translational modification presumed resulting from ubiquitination of the parent protein IPP2K.

TABLE 5

Assignment of Peptide Sequence To Differentially Expressed Urinary Peptides

| Mass (m/z) | Parent Protein | Abundance Change In Cases | Peptide |
| --- | --- | --- | --- |
| 1838.851 | Inositol-1,3,4,5,6-pentakisphosphate 2-kinase | I | E.WGYHGEGNKSLVVAHA.Q + GlyGly (k) (SEQ ID NO: 71) |
| 1190.633 | FAT tumor suppressor 2 | I | S.PEFQQHLYE.A (SEQ ID NO: 65) |
| 983.535 | Zona occludens 3 | I | G.VSSQNLSLN.D (SEQ ID NO: 62) |

I = increased in RFD
Peptide sequence tags assignments for masses determined to be significant using presence-absence analyses or Spearman correlation analyses.

Example 6

Changes in Urine Expression of Intact IPP2K

We examined if intact IPP2K was present and also differentially expressed in case and control urine protein samples. In preparing samples for peptidomic analysis, we had isolated a fraction containing proteins with molecular size >10,000 Da. These samples were then resolved by 10% SDS-PAGE and IPP2K was identified by immunoblot.

Figure 2:
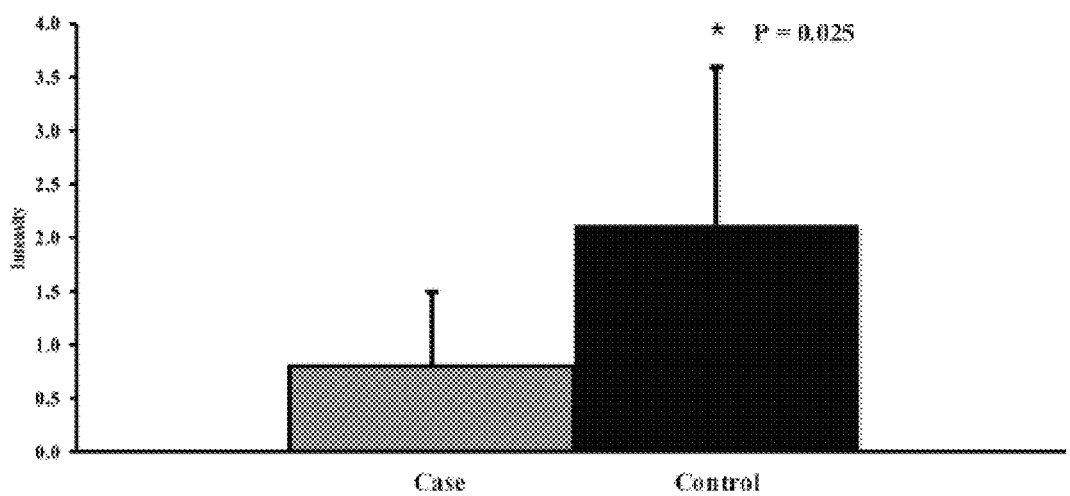
FIG. 2 is a graph showing Immunoblots for IPP2K showed increased urinary expression in cases over control urine samples. Shown are pooled data of immunoblots analyzed by densitometry (Cases, n=8, Controls, n=8).

As show in FIG. 2, IPP2K was detectable in urine and was approximately 2.6 times greater in patients with ERFD who subsequently developed advanced chronic kidney disease.

Example 7

Changes in IPP2K Expression in the Intact Kidney

We examined whether urinary peptide levels might provide insight into disease-induced changes in renal protein expression. We first analyzed IPP2K expression in kidneys from normal and diabetic patients by immunohistochemistry. In keeping with our focus on ERFD for these examples, we analyzed biopsies from diabetic patients with minimal albuminuria and serum creatinine levels of 1.2 to 1.9 mg/dl.

Figure 3:
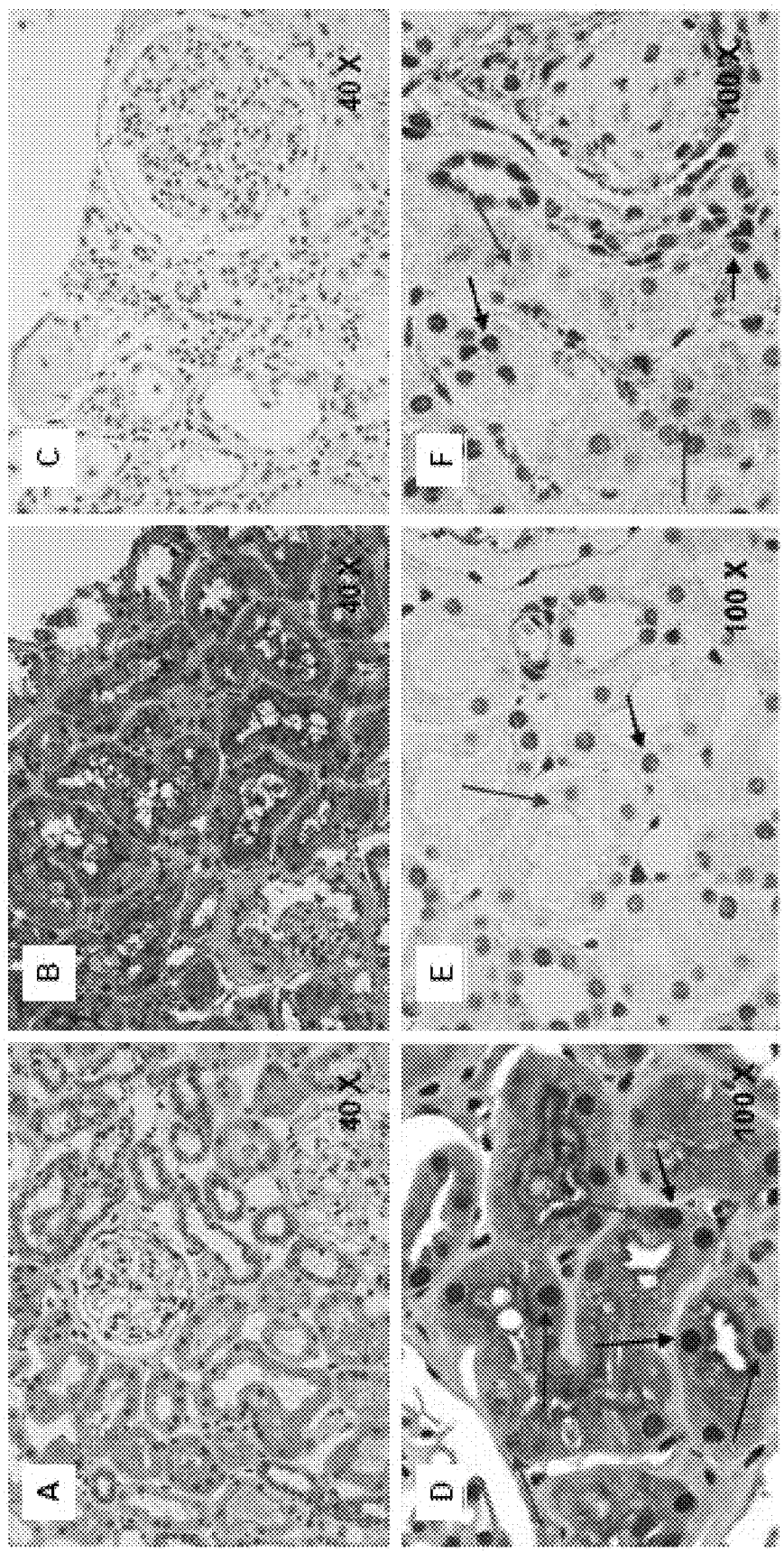
FIGS. 3A-3F are photomicrographs showing IPP2K renal expression is increased in the urine of microalbuminuric type-diabetics with early progressive renal function decline and in the renal parenchyma of type-1 diabetics with minimal nephropathy. Quantitative IPP2K IB analysis demonstrated increased urinary expression in MA T1D cases over MA T1D control urine samples (3A). Immunohistochemical localization of IPP2K in a control kidney biopsy specimen (3B), T1D biopsy specimen (3C) and secondary antibody negative control (3D) demonstrates increased renal tubular cytoplasmic, nuclear, and perinuclear IPP2K staining within the diabetic phenotype. Further single antibody labeling experiments for IPP2K (3E) and TIAR (3F) were conducted in T1D biopsy specimens. Black arrows identify regions of nuclear staining. Grey arrows identify regions of punctate cytoplasmic staining. Unless otherwise noted the presented image is at a 40× magnification.

Shown in FIG. 3 are representative images from six pairs of experiments that examined IPP2K expression in kidneys from normal patients (FIG. 3A), a patient with early DN (FIG. 3B) and negative control for non-specific binding (FIG. 3D). Patients with DN had increased IPP2K expression in renal tubules and glomeruli. While the majority of increased staining was observed in the cytoplasm, intense areas of staining were noted in nuclei or perinuclear areas.

Example 8

IPP2K is Present in Cytoplasmic Granules in Diabetic Nephropathy

IPP2K has been shown recently to be a constituent of mRNA-containing granules responsible for protein translation arrest in stressed cells (9). These cytoplasmic inclusions, referred to as stress granules, are observed in cells subjected to environmental stress including heat, irradiation, oxidative conditions and hyperosmolarity (10). Based on our findings of increased renal and urinary IPP2K in ERFD, we examined if DN was associated with the formation of stress granules.

Shown in FIG. 3D is a 100× magnification image of DN kidney stained for IPP2K. Increased IPP2K staining is seen throughout and is strongly localized in cytoplasmic granules. IPP2K was strongly expressed in nuclei or peri-nuclear areas. We also used immunohistochemistry to determine expression of another protein marker of stress granules, T-cell intracellular antigen-1 related protein (TIAR). Shown in FIG. 3 are sections stained for TIAR from normal kidney (3E) or early diabetic nephropathy (3F). We observed increased TIAR staining in diabetic nephropathy. TIAR was primarily localized to the cytoplasm and in a granular pattern indicative of stress granules.

Example 9

Changes in ZO-3 Expression in the Intact Kidney

Figure 4A:
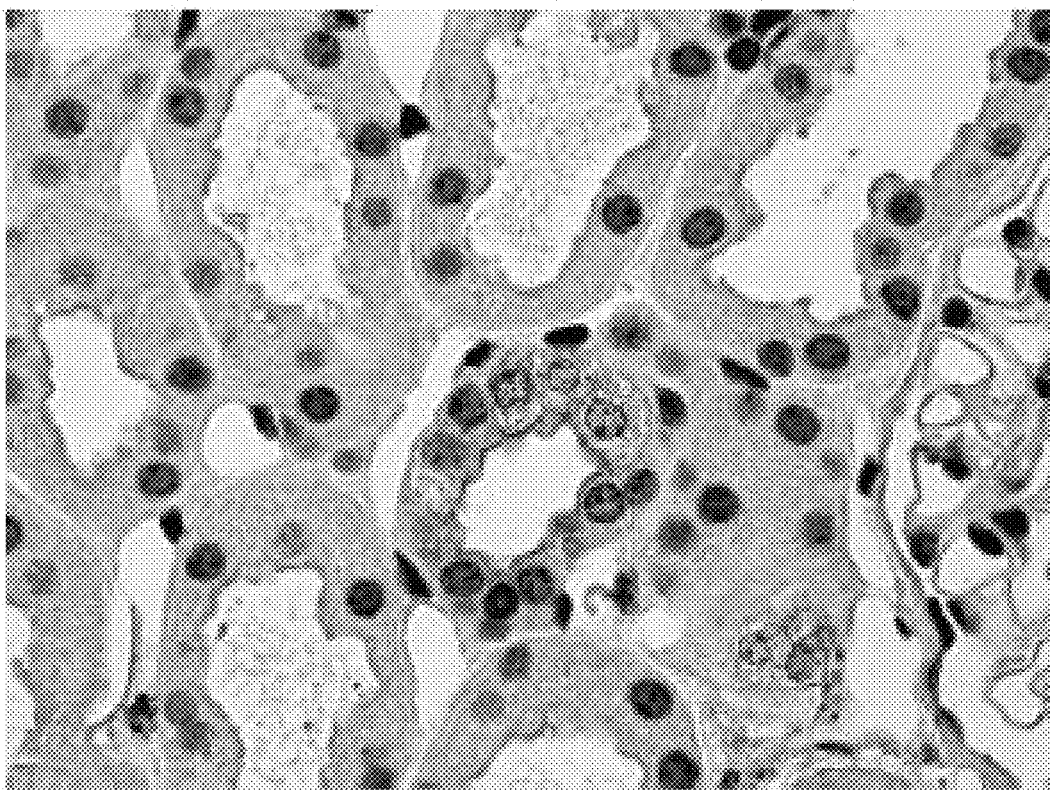
FIGS. 4A and 4B are photomicrographs showing cytoplasmic ZO-3 expression and cell junction staining is increased in renal biopsies of diabetics with minimal nephropathy. Control (4A) and diabetic (4B) renal biopsy sections stained for ZO-3 demonstrated enhanced staining for ZO-3 in the cytoplasm of diabetic biopsy sections and prominent, dense staining in the apical membrane of renal proximal tubular cells and in sites cell to cell interaction within renal tubules and were taken to be diagnostic of tubular adherens junctions.
Figure 4B:
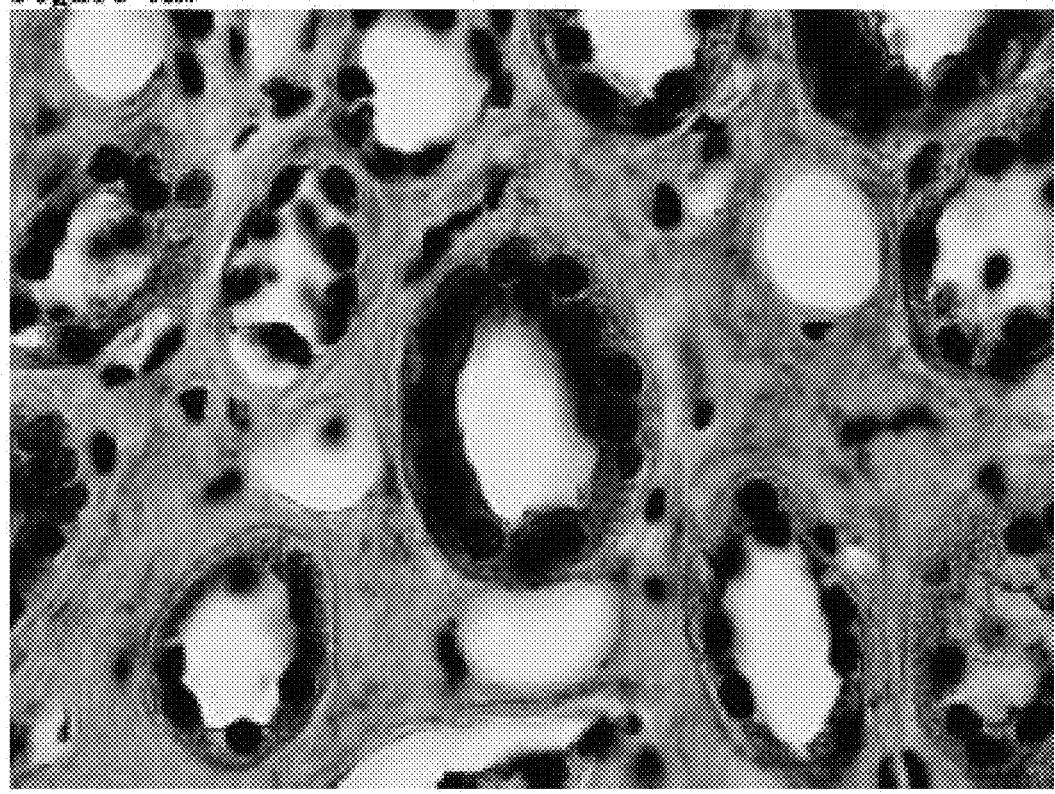

To further examine if urine peptide changes may reflect alterations in intact kidney proteins, we analyzed ZO-3 expression in kidneys from normal and diabetic patients by immuno-histochemistry. We used the same biopsies, studied above, from diabetic patients with minimal albuminuria and serum creatinine levels of 1.2 to 1.9 mg/dl. As shown in FIG. 4, ZO-3 expression was increased in biopsies from patients with DN (4B) when compared to controls (4A). We also observed that ZO-3 staining was less linear, not confined to the cell periphery and increased in the cytoplasm when compared to normals.

Discussion of Examples 2-9

Our goal in these examples was to identify urinary peptides that are associated specifically with the risk of kidney diseases including ERFD, an early phenotype that indicates the initiation of renal function loss while GFR is still in the normal range and while MA is present. Urine samples available in this study were unique: They were taken from subjects early after the development of MA, and could be classified into cases and controls according to their future changes in renal function. As such, the samples could be used to measure peptides that may discriminate those that retain stable renal function from those with ERFD. We reasoned if such discriminating peptides could be identified that they would be specific for ERFD and might provide new insights into the pathophysiology the initiation of renal function loss—as opposed to the onset of MA—and could serve as candidate biomarkers in future studies. We focused on 4 identified peptides for these examples. Each was more abundant in the urine of cases as compared to the urine of well-matched controls. MS sequence tag analysis identified individual peptide fragments of derived from the tight junction protein-3/ZO-3, FAT-2 and IPP2K. The novel findings in these examples include that changes in renal protein expression in diabetes are reflected in the urinary peptidome and occur very early in DN. Secondly, based on the urine peptidomic analysis, we were able to determine that intact IPP2K protein is increased in diabetic kidney and is present in stress granules not observed in normal kidney.

Based on the differential expression of an IPP2K urinary fragment in case and control samples, we examined whether this protein was differentially regulated in normal kidneys and those from patients with T1D. We observed increased expression of IPP2K in renal tubules of patients with T1D compared to normal kidney. Increased IPP2K expression was observed both in nuclei and in the cytoplasm. This finding suggests a hitherto unrecognized role for IPP2K in the damaged kidney or in kidneys responding to stress. IPP2K may have several possible roles in DN. Higher inositol phosphate production proceeds through the action of a IP5/6-kinase to produce Ins(1,3,4,6)P4 which in turn is acted on by a IP5-kinase to produce Ins(1,3,4,5,6)P5, that is then modified by IPP2K to produce InsP6 (11, 12). The role in renal cell function of IPP2K is incompletely understood and the actions of InsP6, the primary product of IPP2K activity, are a focus of considerable interest. One major role for IPP2K has been in the regulation of mature messenger RNA nuclear export and mRNA translation arrest during cellular stress (13). Most recently, cytoplasmic IPP2K has been associated with stress granule formation. Stress granules are phase-dense cytoplasmic particles that appear in eukaryotic cells exposed to environmental stress (e.g. oxidative conditions, hyperosmolarity, nutrient deprivation and UV irradiation). Stress granule assembly is a consequence of abortive translational initiation. If the stress is relieved, the stress granules disassemble, and translation resumes. The persistence of stress granules is considered a reflection of ongoing insults that, if left unchecked, may lead to apoptotic cell death. We observed evidence of stress granules in kidneys with early diabetic nephropathy, as well as in other renal diseases, suggesting that stress-induced changes in translation had occurred.

We also observed that increased amounts of urine peptides derived from the ZO-3 protein reflected changes in the diabetic kidney. Diabetic kidneys had increased tubule cell ZO-3 expression and apparent translocation of the protein from the cell membrane to cytoplasm. ZO-3 is a member of the zona occludens protein family found in epithelial cell apical junction complexes (14). Zona occludens proteins play an important role in maintaining barrier integrity formed by epithelial cells and loss of ZO-3 in particular results in increased permeability of cell layers (15). Recently, Sharma et al. have shown glucose causes translocation of ZO-1 from the cell membrane to the cytoplasm in cultured podocytes (16). Similarly, we observed increased cytoplasmic and decreased membrane ZO-3 staining in renal tubules in human diabetic kidneys. These data indicate that increased ZO-3 fragments in the urine may be a result of the diabetes-induced change in ZO-3 cellular distribution.

In summary, we have identified peptides in the low molecular fraction of urine that correlate with early renal function decline in Type-1 diabetes mellitus. These peptides reflect changes in both tubular and glomerular protein expression that are associated with the formation of stress granules and may define a new cellular mechanism by which diabetic nephropathy is initiated or progresses. Thus, urine peptide expression can provide insight into renal pathophysiologic mechanisms.

Example 10

This Example provides comparison of peptide profiles of plasma samples collected from type-1 diabetic individuals prior to the onset of significant renal function decline. It was determined that discernable changes in the plasma peptidome accompany early progressive renal function decline in type-1 diabetics with microalbuminuria.

Longitudinal patient study allowed for stratification of patient renal function into two groups: significant renal function decline (case) and age-equivalent renal function decline (control). Peptide profiles generated using liquid chromatography (LC), robotic fraction collection, and matrix assisted laser desorption ionization-time of flight mass spectrometry (MALDI-TOF MS) were compared using class discovery and class differentiation methods.

A total of 213 peptide masses out of >9,000 peptide masses were identified as being differentially present to some degree between case and control groups. Manual review of the data allowed for rank ordering of peptide importance based on apparent abundance within samples. Peptides having significant abundance (e.g. a signal to noise (s/n) ratio $\geq 50$) were selected for further studies dedicated to identifying the peptide's amino acid sequence.

Initial analysis provided sixty-three (63) peptides were significant by univariate t-test analysis at the $p<0.01$ significance level. Thirty-two (32) peptides classified patient group samples with case sensitivity (0.5), specificity (0.882) and positive (0.8) and negative (0.652) predictive values. Forty-one (41) peptide sequence tags involving twenty two (22) proteins were identified. A complete listing of plasma peptide biomarkers associated with kidney disease is provided in Table 2 (e.g., SEQ ID NOS: 80-118). In conclusion, the plasma peptidome significantly differs between T1D with MA that do and do not succumb to ERFD. In addition, the difference between the plasma peptidome's of T1D with MA with ERFD and T1D with MA but without ERFD is exhibited months to years in advance of any significant renal function decline.

Example 11

Summary: The experiments noted in Example 10 identified eight peptide sequences as derived from the biologically important peptide bradykinin including one apparently previously-unknown variant of bradykinin. Bradykinin, a proteolytic fragment of the protein kininogen, and differential expression of bradykinin receptors (B1KR and B2KR) are of known significant importance to renal function (Tan et al., (2007) Am J Physiol Renal Physiol. 293(4):F1026-35.).

Differential plasma expression of the bradykinin parent protein, kininogen, has been established in the data of the present example using immunoblot analysis of early progressive renal function decline phenotypic extremes.

A question addressed by the present example was "are the urinary peptides identified as differentially abundant in case versus control patients actually filtered from the plasma through the glomerulus into the urine". We were able to demonstrate that none of the significant urinary peptides originated from the plasma. The analysis of LC-MS data from these 33 plasma samples (n=16 case; n=17 control) identified 63 peptides to be significantly difference between case and control groups by t-test ($p<0.05$); eight of these peptides were fragments of high molecular weight kininogen. From these observations we developed the following hypothesis: The presence of increased amounts of specific peptide fragments of high molecular weigh kininogen (HK) in the case patient plasma as compared the control patient plasma would reflect changes in the amount of the corresponding intact protein in the plasma.

Background: Two splice variants of kininogen occur with the larger variant referred to as high molecular weight kininogen (HK) and the smaller variant referred to low molecular weight kininogen (LK). HK contains six protein domains including protease inhibitor domains, a cytokeratin binding domain, a gC1qR binding domain, a prekallikrein/Factor XI binding domain, and a domain containing the peptide hormone bradykinin (BK). BK is released from HK primarily by the proteolytic activity of plasma kallikrein. BK binds to the constitutively expressed bradykinin-1 receptor (B1R), a G-protein coupled receptor. BK can be degraded by a number of metalloproteinases including the protease, Kininase II also known as angiotensin (AT) converting enzyme (ACE). Interestingly ACE has a higher affinity for BK than for AT. ACE inhibitors are used to treat hypertension in hypertensive diabetics and have a beneficial side effect of reducing proteinuria. Some people ascribe the beneficial effects of ACE inhibitors to the resulting increase in BK half-life and resulting increase in effective tissue BK concentration. The proteolysis of LK by tissue kallikrein releases decapeptide known as kalladin and corresponds to BK plus an additional N-terminal lysine (also known as Lys-bradykinin). BK and kalladin are both proteolytically degraded by enzymes in the kidney and yield the hepta-, hexa-, and penta-polypeptides which were observed in the low molecular proteomic studies conducted in our preliminary studies. The release of BK from HK yields a heavy chain having a molecular weight range of approximately 68,000 to 65,000 Daltons and a light chain having a molecular weight of approximately 58,000 Daltons; subsequently the light chain is further degraded to fragments with a mass range of 49,000 to 42,000 Daltons. The two chains are held together by a single disulfide bond. The heavy chain contains multiple N-linked glycan structures and the light chain contains multiple O-linked glycan structures. Therefore, the differential abundance of BK peptides and BK degradation products should be reflected by the differential abundance of kininogen heavy chain and light chain proteins in the plasma of case versus control patients.

Methods: In order to examine if the increased plasma abundance of kininogen fragments was the result of increased kininogen protein expression, immunoblotting experiments using reduced and denatured plasma protein samples were conducted. The plasma samples were enriched for low abundant proteins including kininogen by depleting albumin using albumin-specific antibody methods (VivaScience, Sartorius, Germany). Samples were prepared using 10 µg of depleted plasma proteins dissolved in Laemmli buffer, separated using 10% NuPAGE gels at 200V constant and electroblotted onto 0.45 µm nitrocellulose. The blocked membrane was immunoblotted using rabbit anti-high molecular weight kininogen polyclonal antibodies in Odyssey infrared imaging blocking buffer (Licor, Lincoln, Nebr.) supplemented with 0.1% Tween 20. Proteins were visualized by incubation of membranes with fluorescent-tagged anti-rabbit antibodies (Molecular Probes, Carlsbad, Calif.) and scanning on an Odyssey infrared imager (Licor).

Figure 5:
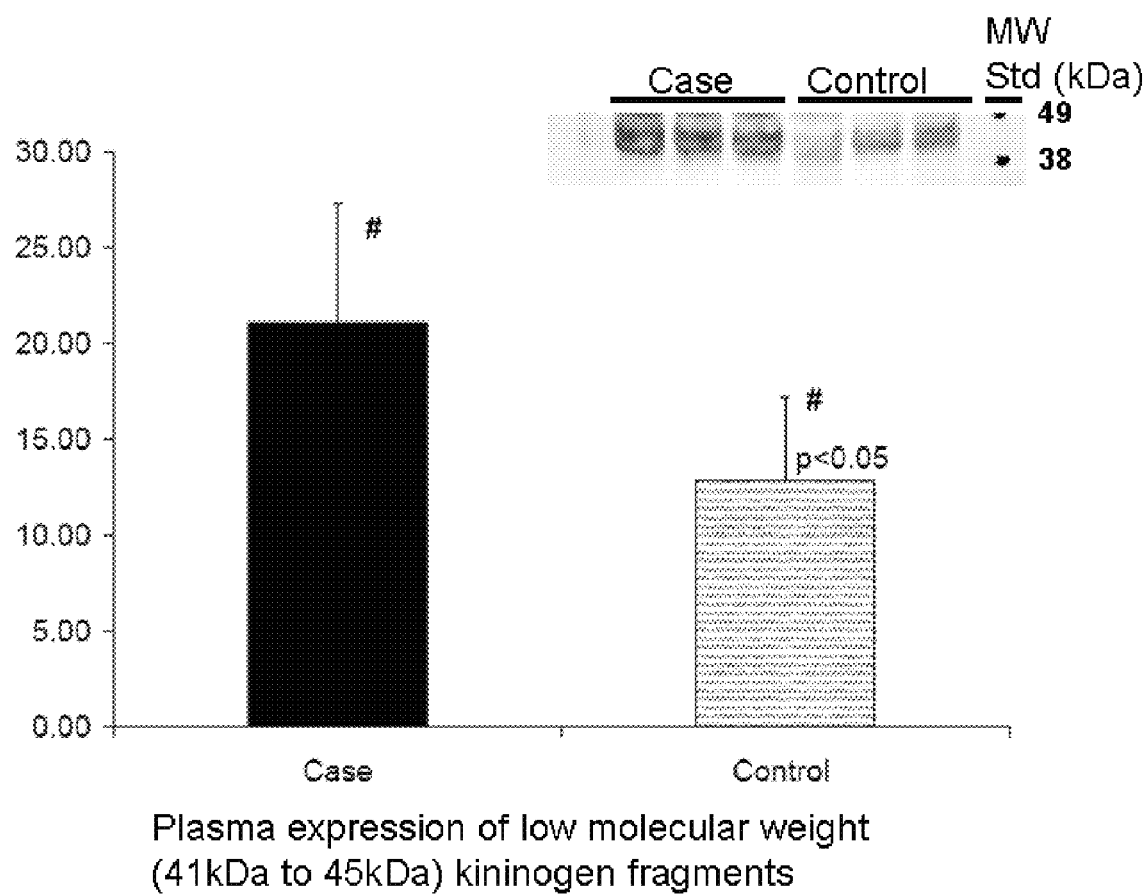
FIG. 5 is a graph showing analysis of low molecular weight (41 kDa to 45 kDa) fragment expression in the plasma of case and control phenotypic extreme samples (n=6). Statistically significant differences at p<0.05 between case and control samples. Insert-representative kininogen IB for case (n=3) and control (n=3) samples.
Figure 6:
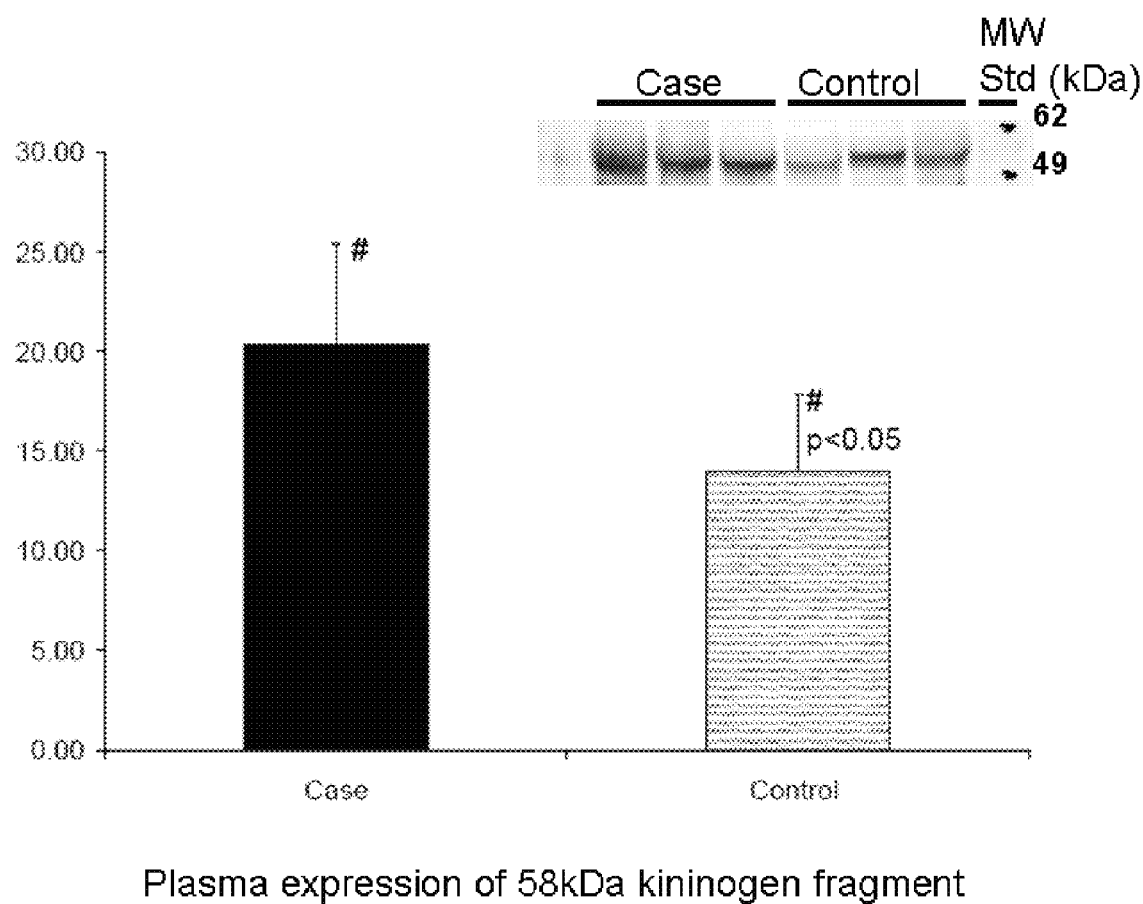
FIG. 6 is a graph showing analysis of HMWK (58 kDa) fragment expression in the plasma of case and control phenotypic extreme samples (n=6). Significant differences at p<0.05 between case and control samples. Insert-representative kininogen IB for case (n=3) and control (n=3) samples.

Results: Immunoblot experiments were conducted using polyclonal antibodies to high molecular weight kininogen. The samples selected for these experiments were composed of the phenotypic extremes (the patients who through 12-20 years longitudinal follow-up demonstrated the most (case) and least (control) severe loss of renal function). These immunoblot experiments identified multiple immunopositive bands migrating at molecular weight ranges between approximately 56,000 and 38,000 Daltons. Data are presented for the analysis of case (n=3) and control (n=3) samples for the bands migrating between 49,000 and 38,000 Daltons (FIG. 5) and a single band migrating between 65,000 and 49,000 Daltons (FIG. 6). From these data and an additional three samples a Pearson analysis for the correlation of band intensities with the estimated rates of renal function decline computed a correlation coefficient of 0.8. The strength of this correlation coefficient suggests that kininogen metabolism is dysregulated between T1D MA individuals with and without early progressive renal function decline.

REFERENCES

1. Mogensen, C. E., Keane, W. F., Bennett, P. H., Jerums, G., Parving, H. H., Passa, P., Steffes, M. W., Striker, G. E. & Viberti, G. C. (1995) *Lancet* 346, 1080-4.
2. Viberti, G. C., Hill, R. D., Jarrett, R. J., Argyropoulos, A., Mahmud, U. & Keen, H. (1982) *Lancet* 1, 1430-2.
3. Perkins, B. A. & Krolewski, A. S. (2005) *Curr Diab Rep* 5, 455-63.
4. Giorgino, F., Laviola, L., Cavallo Perin, P., Solnica, B., Fuller, J. & Chaturvedi, N. (2004) *Diabetologia* 47, 1020-8.
5. Perkins, B. A., Ficociello, L. H., Silva, K. H., Finkelstein, D. M., Warram, J. H. & Krolewski, A. S. (2003) *N. Engl. J. Med.* 348, 2285-2293.
6. Araki, S., Haneda, M., Sugimoto, T., (sono, M., Isshiki, K., Kashiwagi, A. & Koya, D. (2005) *Diabetes* 54, 2983-7.
7. Perkins, B. A., Ficociello, L. H., Ostrander, B. E., Silva, K. H., Weinberg, J., Warram, J. H. & Krolewski, A. S. (2007) *J Am Soc Nephrol* 18, 1353-61.
8. Perkins, B. A., Nelson, R. G., Ostrander, B. E., Blouch, K. L., Krolewski, A. S., Myers, B. D. & Warram, J. H. (2005) *J. Am. Soc. Nephrol.* 16, 1404-1412.
9. Brehm, M. A., Schenk, T. M., Zhou, X., Fanick, W., Lin, H., Windhorst, S., Nalaskowski, M. M., Kobras, M., Shears, S. B. & Mayr, G. W. (2007) *Biochem J.*
10. Anderson, P. & Kedersha, N. (2006) *J Cell Biol* 172, 803-8.
11. Verbsky, J. W., Wilson, M. P., Kisseleva, M. V., Majerus, P. W. & Wente, S. R. (2002) *J Biol Chem* 277, 31857-62.
12. Verbsky, J. W., Chang, S. C., Wilson, M. P., Mochizuki, Y. & Majerus, P. W. (2005) *J Biol Chem* 280, 1911-20.
13. Alcazar-Roman, A. R., Tran, E. J., Guo, S. & Wente, S. R. (2006) *Nat Cell Biol* 8, 711-6.

14. Wang, Q. & Margolis, B. (2007) *Kidney Int* 72, 1448-58.
15. Kiener, T. K., Selptsova-Friedrich, I. & Hunziker, W. (2008) *Dev Biol* 316, 36-49.
16. Sharma, K., Ramachandrarao, S., Qiu, G., Usui, H. K., Zhu, Y., Dunn, S. R., Ouedraogo, R., Hough, K., McCue, P., Chan, L., Falkner, B. & Goldstein, B. J. (2008) *J Clin Invest*.
17. Lindeman, R. D., Tobin, J. & Shock, N. W. (1985) *J Am Geriatr Soc* 33, 278-85.

It will be understood that various details of the presently disclosed subject matter can be changed without departing from the scope of the subject matter. Furthermore, the foregoing description is for the purpose of illustration only, and not for the purpose of limitation.

---

What is claimed is:

1. A method for diagnosing a kidney disease, or the risk thereof, in a subject in need thereof, comprising:
   (a) determining an amount of at least one peptide selected from the group consisting of SEQ ID NOS: 93-95 in a biological sample including a biological fluid or a biological tissue from the subject; and
   (b) comparing the amount of the at least one peptide in the sample with a control level, wherein if the amount determined in (a) is different than the control level, the subject is diagnosed as having, or at an increased risk of developing, the kidney disease.

2. The method of claim 1, wherein determining the amount of the at least one peptide comprises determining the amount of the at least one peptide in the sample using mass spectrometry (MS) analysis, immunoassay analysis, or both.

3. The method of claim 2, wherein the MS analysis comprises matrix-assisted laser desorption/ionization (MALDI) time-of-flight (TOF) MS analysis or electrospray ionization (ESI) MS.

4. The method of claim 3, wherein the MALDI-TOF MS analysis is direct-spot MALDI-TOF or liquid chromatography MALDI-TOF mass spectrometry analysis.

5. The method of claim 2, wherein the immunoassay analysis comprises an enzyme-linked immunosorbent assay (ELISA).

6. The method of claim 1, wherein the at least one peptide is a plurality of peptides.

7. The method of claim 1, wherein the biological sample is a urine sample.

8. The method of claim 1, wherein the biological sample is a blood sample.

9. The method of claim 1, wherein the subject is human.

10. The method of claim 1, wherein the subject is a diabetic subject.

11. The method of claim 10, wherein the kidney disease is diabetic nephropathy.

12. The method of claim 1, further comprising, modifying or prescribing a suitable treatment if the subject is diagnosed as having or at an increased risk of developing the kidney disease.

* * * * *

SEQUENCE LISTING

```
<160> NUMBER OF SEQ ID NOS: 118

<210> SEQ ID NO 1
<211> LENGTH: 9
<212> TYPE: PRT
<213> ORGANISM: Homo sapiens
<220> FEATURE:
<221> NAME/KEY: Oxidation
<222> LOCATION: (7)..(7)
<223> OTHER INFORMATION: Oxidation of sulfur on methionine side chain

<400> SEQUENCE: 1

Pro Gly Asn Pro Gly Asn Met Met Phe
1               5

<210> SEQ ID NO 2
<211> LENGTH: 10
<212> TYPE: PRT
<213> ORGANISM: Homo sapiens

<400> SEQUENCE: 2

Ser Ser Thr Pro Leu Pro Pro Asp Gly Thr
1               5                   10

<210> SEQ ID NO 3
<211> LENGTH: 11
<212> TYPE: PRT
<213> ORGANISM: Homo sapiens

<400> SEQUENCE: 3

Gly Val Ser Ser Gln Asn Leu Ser Leu Asn Asp
1               5                   10

<210> SEQ ID NO 4
<211> LENGTH: 15
<212> TYPE: PRT
<213> ORGANISM: Homo sapiens

<400> SEQUENCE: 4

Ile Gly Pro Ile Gly Pro Ile Gly Pro Thr Gly Pro Ala Ala Pro
1               5                   10                  15

<210> SEQ ID NO 5
<211> LENGTH: 13
<212> TYPE: PRT
<213> ORGANISM: Homo sapiens

<400> SEQUENCE: 5

Ile Ile Ala Asp Arg Pro Gly Leu Pro Gly Pro Glu His
1               5                   10

<210> SEQ ID NO 6
<211> LENGTH: 11
<212> TYPE: PRT
<213> ORGANISM: Homo sapiens

<400> SEQUENCE: 6
```

```
Ser Pro Glu Phe Gln Gln His Leu Tyr Glu Ala
1               5                   10

<210> SEQ ID NO 7
<211> LENGTH: 15
<212> TYPE: PRT
<213> ORGANISM: Homo sapiens

<400> SEQUENCE: 7

Leu Pro Gly Pro Lys Gly Ser Pro Gly Ser Val Gly Leu Lys Gly
1               5                   10                  15

<210> SEQ ID NO 8
<211> LENGTH: 14
<212> TYPE: PRT
<213> ORGANISM: Homo sapiens
<220> FEATURE:
<221> NAME/KEY: Hydroxyl group
<222> LOCATION: (6)..(6)
<223> OTHER INFORMATION: Hydroxyl group
<220> FEATURE:
<221> NAME/KEY: Hydroxyl group
<222> LOCATION: (12)..(12)
<223> OTHER INFORMATION: Hydroxyl group

<400> SEQUENCE: 8

Pro Gly Leu Pro Gly Pro Pro Gly Pro Met Asp Pro Asn Leu
1               5                   10

<210> SEQ ID NO 9
<211> LENGTH: 18
<212> TYPE: PRT
<213> ORGANISM: Homo sapiens
<220> FEATURE:
<221> NAME/KEY: Hydroxyl group
<222> LOCATION: (3)..(3)
<223> OTHER INFORMATION: Hydroxyl group
<220> FEATURE:
<221> NAME/KEY: Hydroxyl group
<222> LOCATION: (9)..(9)
<223> OTHER INFORMATION: Hydroxyl group
<220> FEATURE:
<221> NAME/KEY: Hydroxyl group
<222> LOCATION: (15)..(15)
<223> OTHER INFORMATION: Hydroxyl group

<400> SEQUENCE: 9

Gly Ser Pro Gly Ser Asn Gly Ala Pro Gly Gln Arg Gly Glu Pro Gly
1               5                   10                  15

Pro Gln

<210> SEQ ID NO 10
<211> LENGTH: 17
<212> TYPE: PRT
<213> ORGANISM: Homo sapiens

<400> SEQUENCE: 10

Thr Lys Leu Lys Lys Thr Pro Thr Glu Ala Pro Ala Asp Cys Arg Ala
1               5                   10                  15

Leu

<210> SEQ ID NO 11
<211> LENGTH: 22
<212> TYPE: PRT
<213> ORGANISM: Homo sapiens
<220> FEATURE:
<221> NAME/KEY: Hydroxyl group
<222> LOCATION: (4)..(4)
```

```
<223> OTHER INFORMATION: Hydroxyl group
<220> FEATURE:
<221> NAME/KEY: Hydroxyl group
<222> LOCATION: (9)..(9)
<223> OTHER INFORMATION: Hydroxyl group
<220> FEATURE:
<221> NAME/KEY: Hydroxyl group
<222> LOCATION: (10)..(10)
<223> OTHER INFORMATION: Hydroxyl group
<220> FEATURE:
<221> NAME/KEY: Hydroxyl group
<222> LOCATION: (21)..(21)
<223> OTHER INFORMATION: Hydroxyl group

<400> SEQUENCE: 11

Gln Gly Leu Pro Gly Thr Gly Gly Pro Pro Gly Glu Asn Gly Lys Pro
1               5                   10                  15

Gly Glu Pro Gly Pro Lys
            20

<210> SEQ ID NO 12
<211> LENGTH: 18
<212> TYPE: PRT
<213> ORGANISM: Homo sapiens
<220> FEATURE:
<221> NAME/KEY: Glycine-Glycine
<222> LOCATION: (10)..(10)
<223> OTHER INFORMATION: Glycine-Glycine dipeptide addition to the side
      chain epsilon amino group of lysine

<400> SEQUENCE: 12

Glu Trp Gly Tyr His Gly Glu Gly Asn Lys Ser Leu Val Val Ala His
1               5                   10                  15

Ala Gln

<210> SEQ ID NO 13
<211> LENGTH: 27
<212> TYPE: PRT
<213> ORGANISM: Homo sapiens
<220> FEATURE:
<221> NAME/KEY: Hydroxyl group
<222> LOCATION: (4)..(4)
<223> OTHER INFORMATION: Hydroxyl group
<220> FEATURE:
<221> NAME/KEY: Hydroxyl group
<222> LOCATION: (16)..(16)
<223> OTHER INFORMATION: Hydroxyl group
<220> FEATURE:
<221> NAME/KEY: Hydroxyl group
<222> LOCATION: (19)..(19)
<223> OTHER INFORMATION: Hydroxyl group
<220> FEATURE:
<221> NAME/KEY: Hydroxyl group
<222> LOCATION: (25)..(25)
<223> OTHER INFORMATION: Hydroxyl group

<400> SEQUENCE: 13

Asn Gly Ala Pro Gly Asn Asp Gly Ala Lys Gly Asp Ala Gly Ala Pro
1               5                   10                  15

Gly Ala Pro Gly Ser Gln Gly Ala Pro Gly Leu
            20                  25

<210> SEQ ID NO 14
<211> LENGTH: 24
<212> TYPE: PRT
<213> ORGANISM: Homo sapiens
<220> FEATURE:
<221> NAME/KEY: Hydroxyl group
<222> LOCATION: (4)..(4)
<223> OTHER INFORMATION: Hydroxyl group
<220> FEATURE:
```

```
<221> NAME/KEY: Hydroxyl group
<222> LOCATION: (8)..(8)
<223> OTHER INFORMATION: Hydroxyl group
<220> FEATURE:
<221> NAME/KEY: Hydroxyl group
<222> LOCATION: (11)..(11)
<223> OTHER INFORMATION: Hydroxyl group

<400> SEQUENCE: 14

Ser Pro Gly Pro Trp Gly Ala Pro Gly Leu Pro Gly Glu Lys Gly Asp
1               5                   10                  15

His Gly Phe Pro Gly Ser Ser Gly
            20

<210> SEQ ID NO 15
<211> LENGTH: 25
<212> TYPE: PRT
<213> ORGANISM: Homo sapiens
<220> FEATURE:
<221> NAME/KEY: Hydroxyl group
<222> LOCATION: (8)..(8)
<223> OTHER INFORMATION: Hydroxyl group
<220> FEATURE:
<221> NAME/KEY: Hydroxyl group
<222> LOCATION: (21)..(21)
<223> OTHER INFORMATION: Hydroxyl group

<400> SEQUENCE: 15

Gly Lys Asn Gly Glu Tyr Gly Pro Gln Gly Pro Pro Gly Pro Thr Gly
1               5                   10                  15

Pro Gly Gly Asp Lys Gly Asp Thr Gly
            20                  25

<210> SEQ ID NO 16
<211> LENGTH: 26
<212> TYPE: PRT
<213> ORGANISM: Homo sapiens
<220> FEATURE:
<221> NAME/KEY: Hydroxyl group
<222> LOCATION: (18)..(18)
<223> OTHER INFORMATION: Hydroxyl group
<220> FEATURE:
<221> NAME/KEY: Hydroxyl group
<222> LOCATION: (23)..(23)
<223> OTHER INFORMATION: Hydroxyl group

<400> SEQUENCE: 16

Gly Pro Lys Gly Arg Gly Gly Pro Asn Gly Asp Pro Gly Pro Leu Gly
1               5                   10                  15

Pro Pro Gly Glu Lys Gly Lys Leu Gly Val
            20                  25

<210> SEQ ID NO 17
<211> LENGTH: 23
<212> TYPE: PRT
<213> ORGANISM: Homo sapiens

<400> SEQUENCE: 17

Leu Leu Ser Asp Pro Glu Gln Gly Val Glu Val Thr Gly Gln Tyr Glu
1               5                   10                  15

Arg Glu Lys Ala Gly Phe Ser
            20

<210> SEQ ID NO 18
<211> LENGTH: 26
<212> TYPE: PRT
<213> ORGANISM: Homo sapiens
<220> FEATURE:
```

```
<221> NAME/KEY: Hydroxyl group
<222> LOCATION: (13)..(13)
<223> OTHER INFORMATION: Hydroxyl group
<220> FEATURE:
<221> NAME/KEY: Hydroxyl group
<222> LOCATION: (16)..(16)
<223> OTHER INFORMATION: Hydroxyl group
<220> FEATURE:
<221> NAME/KEY: Hydroxyl group
<222> LOCATION: (22)..(22)
<223> OTHER INFORMATION: Hydroxyl group

<400> SEQUENCE: 18

Pro Gly Lys Asn Gly Asp Asp Gly Glu Ala Gly Lys Pro Gly Arg Pro
1               5                   10                  15

Gly Glu Arg Gly Pro Pro Gly Pro Gln Gly
            20                  25

<210> SEQ ID NO 19
<211> LENGTH: 22
<212> TYPE: PRT
<213> ORGANISM: Homo sapiens
<220> FEATURE:
<221> NAME/KEY: Hydroxyl group
<222> LOCATION: (17)..(17)
<223> OTHER INFORMATION: Hydroxyl group
<220> FEATURE:
<221> NAME/KEY: Hydroxyl group
<222> LOCATION: (18)..(18)
<223> OTHER INFORMATION: Hydroxyl group

<400> SEQUENCE: 19

Gln Cys Gln Ala Ile Arg Glu Ala Tyr Leu Thr Gln Leu Met Ile Ile
1               5                   10                  15

Lys Asn Ser Thr Tyr Arg
            20

<210> SEQ ID NO 20
<211> LENGTH: 38
<212> TYPE: PRT
<213> ORGANISM: Homo sapiens
<220> FEATURE:
<221> NAME/KEY: Hydroxyl group
<222> LOCATION: (7)..(7)
<223> OTHER INFORMATION: Hydroxyl group
<220> FEATURE:
<221> NAME/KEY: Hydroxyl group
<222> LOCATION: (8)..(8)
<223> OTHER INFORMATION: Hydroxyl group
<220> FEATURE:
<221> NAME/KEY: Hydroxyl group
<222> LOCATION: (17)..(17)
<223> OTHER INFORMATION: Hydroxyl group
<220> FEATURE:
<221> NAME/KEY: Hydroxyl group
<222> LOCATION: (20)..(20)
<223> OTHER INFORMATION: Hydroxyl group
<220> FEATURE:
<221> NAME/KEY: Hydroxyl group
<222> LOCATION: (23)..(23)
<223> OTHER INFORMATION: Hydroxyl group
<220> FEATURE:
<221> NAME/KEY: Hydroxyl group
<222> LOCATION: (28)..(28)
<223> OTHER INFORMATION: Hydroxyl group
<220> FEATURE:
<221> NAME/KEY: Hydroxyl group
<222> LOCATION: (29)..(29)
<223> OTHER INFORMATION: Hydroxyl group

<400> SEQUENCE: 20

Pro Ala Gly Pro Pro Gly Pro Pro Gly Pro Pro Gly Thr Ser Gly His
1               5                   10                  15
```

```
Pro Gly Ser Pro Gly Ser Pro Gly Tyr Gln Gly Pro Pro Gly Glu Pro
            20                  25                  30

Gly Gln Ala Gly Pro Ser
        35

<210> SEQ ID NO 21
<211> LENGTH: 18
<212> TYPE: PRT
<213> ORGANISM: Homo sapiens

<400> SEQUENCE: 21

Thr Ala Asp Ser Gly Glu Gly Asp Phe Leu Ala Glu Gly Gly Gly Val
1               5                   10                  15

Arg Gly

<210> SEQ ID NO 22
<211> LENGTH: 18
<212> TYPE: PRT
<213> ORGANISM: Homo sapiens

<400> SEQUENCE: 22

Thr Ala Asp Ser Gly Glu Gly Asp Phe Leu Ala Glu Gly Gly Gly Val
1               5                   10                  15

Arg Gly

<210> SEQ ID NO 23
<211> LENGTH: 29
<212> TYPE: PRT
<213> ORGANISM: Homo sapiens

<400> SEQUENCE: 23

Lys Met Ala Asp Glu Ala Gly Ser Glu Ala Asp His Glu Gly Thr His
1               5                   10                  15

Ser Thr Lys Arg Gly His Ala Lys Ser Arg Pro Val Arg
            20                  25

<210> SEQ ID NO 24
<211> LENGTH: 29
<212> TYPE: PRT
<213> ORGANISM: Homo sapiens
<220> FEATURE:
<221> NAME/KEY: Oxidation
<222> LOCATION: (2)..(2)
<223> OTHER INFORMATION: Oxidation of sulfur on methionine side chain

<400> SEQUENCE: 24

Lys Met Ala Asp Glu Ala Gly Ser Glu Ala Asp His Glu Gly Thr His
1               5                   10                  15

Ser Thr Lys Arg Gly His Ala Lys Ser Arg Pro Val Arg
            20                  25

<210> SEQ ID NO 25
<211> LENGTH: 9
<212> TYPE: PRT
<213> ORGANISM: Homo sapiens

<400> SEQUENCE: 25

Lys Arg Pro Pro Gly Phe Ser Pro Phe
1               5

<210> SEQ ID NO 26
<211> LENGTH: 10
<212> TYPE: PRT
```

```
<213> ORGANISM: Homo sapiens

<400> SEQUENCE: 26

Lys Arg Pro Pro Gly Phe Ser Pro Phe Arg
1               5                   10

<210> SEQ ID NO 27
<211> LENGTH: 10
<212> TYPE: PRT
<213> ORGANISM: Homo sapiens
<220> FEATURE:
<221> NAME/KEY: Hydroxl group
<222> LOCATION: (4)..(4)
<223> OTHER INFORMATION: Hydroxl group

<400> SEQUENCE: 27

Lys Arg Pro Pro Gly Phe Ser Pro Phe Arg
1               5                   10

<210> SEQ ID NO 28
<211> LENGTH: 10
<212> TYPE: PRT
<213> ORGANISM: Homo sapiens
<220> FEATURE:
<221> NAME/KEY: Hydroxyl group
<222> LOCATION: (8)..(8)
<223> OTHER INFORMATION: Hydroxyl group

<400> SEQUENCE: 28

Lys Arg Pro Pro Gly Phe Ser Pro Phe Arg
1               5                   10

<210> SEQ ID NO 29
<211> LENGTH: 11
<212> TYPE: PRT
<213> ORGANISM: Homo sapiens

<400> SEQUENCE: 29

Lys Arg Pro Pro Gly Phe Ser Pro Phe Arg Lys
1               5                   10

<210> SEQ ID NO 30
<211> LENGTH: 11
<212> TYPE: PRT
<213> ORGANISM: Homo sapiens
<220> FEATURE:
<221> NAME/KEY: Hydroxyl group
<222> LOCATION: (4)..(4)
<223> OTHER INFORMATION: Hydroxyl group
<220> FEATURE:
<221> NAME/KEY: Hydroxyl group
<222> LOCATION: (8)..(8)
<223> OTHER INFORMATION: Hydroxyl group

<400> SEQUENCE: 30

Lys Arg Pro Pro Gly Phe Ser Pro Phe Arg Lys
1               5                   10

<210> SEQ ID NO 31
<211> LENGTH: 10
<212> TYPE: PRT
<213> ORGANISM: Homo sapiens

<400> SEQUENCE: 31

His Asp Trp Gly His Glu Lys Gln Arg Lys
1               5                   10

<210> SEQ ID NO 32
```

```
<211> LENGTH: 19
<212> TYPE: PRT
<213> ORGANISM: Homo sapiens

<400> SEQUENCE: 32

His Asn Leu Gly His Gly His Lys His Glu Arg Asp Gln Gly His Gly
1               5                   10                  15

His Gln Arg

<210> SEQ ID NO 33
<211> LENGTH: 11
<212> TYPE: PRT
<213> ORGANISM: Homo sapiens

<400> SEQUENCE: 33

Met Asn Phe Arg Pro Gly Val Leu Ser Ser Arg
1               5                   10

<210> SEQ ID NO 34
<211> LENGTH: 19
<212> TYPE: PRT
<213> ORGANISM: Homo sapiens

<400> SEQUENCE: 34

Leu Gly Leu Pro Gly Pro Pro Asp Val Pro Asp His Ala Ala Tyr His
1               5                   10                  15

Pro Phe Arg

<210> SEQ ID NO 35
<211> LENGTH: 17
<212> TYPE: PRT
<213> ORGANISM: Homo sapiens

<400> SEQUENCE: 35

Pro Gly Pro Pro Asp Val Pro Asp His Ala Ala Tyr His Pro Phe Arg
1               5                   10                  15

Arg

<210> SEQ ID NO 36
<211> LENGTH: 9
<212> TYPE: PRT
<213> ORGANISM: Homo sapiens

<400> SEQUENCE: 36

Asp His Ala Ala Tyr His Pro Phe Arg
1               5

<210> SEQ ID NO 37
<211> LENGTH: 11
<212> TYPE: PRT
<213> ORGANISM: Homo sapiens
<220> FEATURE:
<221> NAME/KEY: Optional carboxylation
<222> LOCATION: (3)..(3)
<223> OTHER INFORMATION: Optional carboxylation of glutamic acid side
      chain
<220> FEATURE:
<221> NAME/KEY: Optional carboxylation
<222> LOCATION: (6)..(6)
<223> OTHER INFORMATION: Optional carboxylation of glutamic acid side
      chain

<400> SEQUENCE: 37

Gln Asp Glu Gly Ala Glu Pro Leu Lys Gln Arg
1               5                   10
```

-continued

<210> SEQ ID NO 38
<211> LENGTH: 14
<212> TYPE: PRT
<213> ORGANISM: Homo sapiens

<400> SEQUENCE: 38

Arg Asn Gly Phe Lys Ser His Ala Leu Gln Leu Asn Asn Arg
1               5                   10

<210> SEQ ID NO 39
<211> LENGTH: 11
<212> TYPE: PRT
<213> ORGANISM: Homo sapiens
<220> FEATURE:
<221> NAME/KEY: Carboxylation
<222> LOCATION: (2)..(2)
<223> OTHER INFORMATION: Gamma carboxylation of glutamic acid side chain

<400> SEQUENCE: 39

Pro Glu Pro Pro Thr Ser Ala Ser Ile Leu Ser
1               5                   10

<210> SEQ ID NO 40
<211> LENGTH: 12
<212> TYPE: PRT
<213> ORGANISM: Homo sapiens

<400> SEQUENCE: 40

Leu Ile Cys His Thr Gly His Glu Gln Ala Gly Arg
1               5                   10

<210> SEQ ID NO 41
<211> LENGTH: 13
<212> TYPE: PRT
<213> ORGANISM: Homo sapiens

<400> SEQUENCE: 41

Leu Ile Cys His Thr Gly His Glu Gln Ala Gly Arg Glu
1               5                   10

<210> SEQ ID NO 42
<211> LENGTH: 11
<212> TYPE: PRT
<213> ORGANISM: Homo sapiens

<400> SEQUENCE: 42

Asp Asp Asp Met Ser Gly Asp Glu Lys Gln Asp
1               5                   10

<210> SEQ ID NO 43
<211> LENGTH: 10
<212> TYPE: PRT
<213> ORGANISM: Homo sapiens
<220> FEATURE:
<221> NAME/KEY: Carboxylation
<222> LOCATION: (4)..(4)
<223> OTHER INFORMATION: Gamma carboxylation of glutamic acid side chain

<400> SEQUENCE: 43

Tyr Ile Arg Glu Gly His Glu Lys Gln Ala
1               5                   10

<210> SEQ ID NO 44
<211> LENGTH: 10
<212> TYPE: PRT
<213> ORGANISM: Homo sapiens
<220> FEATURE:

```
<221> NAME/KEY: Carboxylation
<222> LOCATION: (7)..(7)
<223> OTHER INFORMATION: Gamma carboxylation of glutamic acid side chain

<400> SEQUENCE: 44

Tyr Ile Arg Glu Gly His Glu Lys Gln Ala
1               5                   10

<210> SEQ ID NO 45
<211> LENGTH: 11
<212> TYPE: PRT
<213> ORGANISM: Homo sapiens

<400> SEQUENCE: 45

Thr Met Ala Glu Ala Ser Glu Asp Ser Pro Arg
1               5                   10

<210> SEQ ID NO 46
<211> LENGTH: 14
<212> TYPE: PRT
<213> ORGANISM: Homo sapiens
<220> FEATURE:
<221> NAME/KEY: Optional hydroxyl group
<222> LOCATION: (4)..(4)
<223> OTHER INFORMATION: Optional hydroxyl group
<220> FEATURE:
<221> NAME/KEY: Optional hydroxyl group
<222> LOCATION: (11)..(11)
<223> OTHER INFORMATION: Optional hydroxyl group

<400> SEQUENCE: 46

Leu Arg Ser Pro Ser Ser Leu Leu His Asp Pro Ala Leu His
1               5                   10

<210> SEQ ID NO 47
<211> LENGTH: 15
<212> TYPE: PRT
<213> ORGANISM: Homo sapiens
<220> FEATURE:
<221> NAME/KEY: Optional hydroxyl group
<222> LOCATION: (2)..(2)
<223> OTHER INFORMATION: Optional hydroxyl group
<220> FEATURE:
<221> NAME/KEY: Optional hydroxyl group
<222> LOCATION: (4)..(4)
<223> OTHER INFORMATION: Optional hydroxyl group
<220> FEATURE:
<221> NAME/KEY: Optional hydroxyl group
<222> LOCATION: (6)..(6)
<223> OTHER INFORMATION: Optional hydroxyl group

<400> SEQUENCE: 47

Ser Pro Thr Pro Arg Pro Arg Met Lys Lys Asp Glu Ser Phe
1               5                   10                  15

<210> SEQ ID NO 48
<211> LENGTH: 10
<212> TYPE: PRT
<213> ORGANISM: Homo sapiens

<400> SEQUENCE: 48

Arg Val Ser Val His Pro Asp Tyr Arg Gln
1               5                   10

<210> SEQ ID NO 49
<211> LENGTH: 13
<212> TYPE: PRT
<213> ORGANISM: Homo sapiens
<220> FEATURE:
<221> NAME/KEY: Carboxylation
```

```
<222> LOCATION: (5)..(5)
<223> OTHER INFORMATION: Gamma carboxylation of glutamic acid side chain
<220> FEATURE:
<221> NAME/KEY: Hydroxyl group
<222> LOCATION: (11)..(11)
<223> OTHER INFORMATION: Hydroxyl group

<400> SEQUENCE: 49

Tyr Thr Asp Ser Glu Ser Ser Ala Ser Leu Pro Arg Ser
1               5                   10

<210> SEQ ID NO 50
<211> LENGTH: 18
<212> TYPE: PRT
<213> ORGANISM: Homo sapiens
<220> FEATURE:
<221> NAME/KEY: Optional hydroxyl group
<222> LOCATION: (12)..(12)
<223> OTHER INFORMATION: Optional hydroxyl group
<220> FEATURE:
<221> NAME/KEY: Optional hydroxyl group
<222> LOCATION: (13)..(13)
<223> OTHER INFORMATION: Optional hydroxyl group
<220> FEATURE:
<221> NAME/KEY: Optional hydroxyl group
<222> LOCATION: (14)..(14)
<223> OTHER INFORMATION: Optional hydroxyl group

<400> SEQUENCE: 50

Asp Arg Arg Thr Gln Glu Gly Gly Arg Gly Asp Pro Pro Pro Ala Gly
1               5                   10                  15

Arg Ser

<210> SEQ ID NO 51
<211> LENGTH: 10
<212> TYPE: PRT
<213> ORGANISM: Homo sapiens

<400> SEQUENCE: 51

Val Asp His Pro Asn Glu Glu Gln Gln Lys
1               5                   10

<210> SEQ ID NO 52
<211> LENGTH: 10
<212> TYPE: PRT
<213> ORGANISM: Homo sapiens
<220> FEATURE:
<221> NAME/KEY: Optional carboxylation
<222> LOCATION: (6)..(6)
<223> OTHER INFORMATION: Optional carboxylation of glutamic acid side
      chain
<220> FEATURE:
<221> NAME/KEY: Optional carboxylation
<222> LOCATION: (7)..(7)
<223> OTHER INFORMATION: Optional carboxylation of glutamic acid side
      chain

<400> SEQUENCE: 52

Val Asp His Pro Asn Glu Glu Gln Gln Lys
1               5                   10

<210> SEQ ID NO 53
<211> LENGTH: 11
<212> TYPE: PRT
<213> ORGANISM: Homo sapiens
<220> FEATURE:
<221> NAME/KEY: Hydroxyl group
<222> LOCATION: (9)..(9)
<223> OTHER INFORMATION: Hydroxyl group

<400> SEQUENCE: 53
```

```
Pro Gly Leu Glu Ser Gly Asp Ile Pro Ser Pro
1               5                   10
```

<210> SEQ ID NO 54
<211> LENGTH: 9
<212> TYPE: PRT
<213> ORGANISM: Homo sapiens

<400> SEQUENCE: 54

```
Leu Pro His Asp Ser Gly Gln Gln His
1               5
```

<210> SEQ ID NO 55
<211> LENGTH: 9
<212> TYPE: PRT
<213> ORGANISM: Homo sapiens
<220> FEATURE:
<221> NAME/KEY: Carboxylation
<222> LOCATION: (3)..(3)
<223> OTHER INFORMATION: Gamma carboxylation of glutamic acid side chain
<220> FEATURE:
<221> NAME/KEY: Hydroxyl group
<222> LOCATION: (6)..(6)
<223> OTHER INFORMATION: Hydroxyl group

<400> SEQUENCE: 55

```
Ser Arg Glu Thr Ser Pro Asn Arg Ile
1               5
```

<210> SEQ ID NO 56
<211> LENGTH: 15
<212> TYPE: PRT
<213> ORGANISM: Homo sapiens
<220> FEATURE:
<221> NAME/KEY: Optional hydroxyl group
<222> LOCATION: (6)..(6)
<223> OTHER INFORMATION: Optional hydroxyl group
<220> FEATURE:
<221> NAME/KEY: Optional hydroxyl group
<222> LOCATION: (7)..(7)
<223> OTHER INFORMATION: Optional hydroxyl group
<220> FEATURE:
<221> NAME/KEY: Optional hydroxyl group
<222> LOCATION: (15)..(15)
<223> OTHER INFORMATION: Optional hydroxyl group

<400> SEQUENCE: 56

```
Arg His Arg Ser His Pro Pro Gly Trp Ala Ser Gly Ala Arg Pro
1               5                   10                  15
```

<210> SEQ ID NO 57
<211> LENGTH: 12
<212> TYPE: PRT
<213> ORGANISM: Homo sapiens
<220> FEATURE:
<221> NAME/KEY: Carboxylation
<222> LOCATION: (5)..(5)
<223> OTHER INFORMATION: Gamma carboxylation of glutamic acid side chain
<220> FEATURE:
<221> NAME/KEY: Hydroxyl group
<222> LOCATION: (6)..(6)
<223> OTHER INFORMATION: Hydroxyl group

<400> SEQUENCE: 57

```
Ala Asn Gly Ala Glu Pro Ser Arg Ala Val Gly Thr
1               5                   10
```

<210> SEQ ID NO 58
<211> LENGTH: 17
<212> TYPE: PRT

```
<213> ORGANISM: Homo sapiens
<220> FEATURE:
<221> NAME/KEY: Hydroxyl group
<222> LOCATION: (8)..(8)
<223> OTHER INFORMATION: Hydroxyl group
<220> FEATURE:
<221> NAME/KEY: Optional carboxylation
<222> LOCATION: (10)..(10)
<223> OTHER INFORMATION: Optional carboxylation of glutamic acid side
      chain
<220> FEATURE:
<221> NAME/KEY: Optional carboxylation
<222> LOCATION: (11)..(11)
<223> OTHER INFORMATION: Optional carboxylation of glutamic acid side
      chain
<220> FEATURE:
<221> NAME/KEY: Hydroxyl group
<222> LOCATION: (14)..(14)
<223> OTHER INFORMATION: Hydroxyl group

<400> SEQUENCE: 58

Ala Arg Thr Asp Glu Val Leu Pro Glu Glu Ala Ala Pro Arg Arg Lys
1               5                   10                  15

Met

<210> SEQ ID NO 59
<211> LENGTH: 17
<212> TYPE: PRT
<213> ORGANISM: Homo sapiens

<400> SEQUENCE: 59

His Tyr Glu Asn Gly Glu Tyr Ile Ile Arg Gln Gly Ala Arg Gly Asp
1               5                   10                  15

Thr

<210> SEQ ID NO 60
<211> LENGTH: 7
<212> TYPE: PRT
<213> ORGANISM: Homo sapiens
<220> FEATURE:
<221> NAME/KEY: Oxidation
<222> LOCATION: (6)..(6)
<223> OTHER INFORMATION: Oxidation of sulfur on methionine side chain

<400> SEQUENCE: 60

Gly Asn Pro Gly Asn Met Met
1               5

<210> SEQ ID NO 61
<211> LENGTH: 8
<212> TYPE: PRT
<213> ORGANISM: Homo sapiens

<400> SEQUENCE: 61

Ser Thr Pro Leu Pro Pro Asp Gly
1               5

<210> SEQ ID NO 62
<211> LENGTH: 9
<212> TYPE: PRT
<213> ORGANISM: Homo sapiens

<400> SEQUENCE: 62

Val Ser Ser Gln Asn Leu Ser Leu Asn
1               5

<210> SEQ ID NO 63
<211> LENGTH: 13
```

```
<212> TYPE: PRT
<213> ORGANISM: Homo sapiens

<400> SEQUENCE: 63

Gly Pro Ile Gly Pro Ile Gly Pro Thr Gly Pro Ala Ala
1               5                   10

<210> SEQ ID NO 64
<211> LENGTH: 11
<212> TYPE: PRT
<213> ORGANISM: Homo sapiens

<400> SEQUENCE: 64

Ile Ala Asp Arg Pro Gly Leu Pro Gly Pro Glu
1               5                   10

<210> SEQ ID NO 65
<211> LENGTH: 9
<212> TYPE: PRT
<213> ORGANISM: Homo sapiens

<400> SEQUENCE: 65

Pro Glu Phe Gln Gln His Leu Tyr Glu
1               5

<210> SEQ ID NO 66
<211> LENGTH: 13
<212> TYPE: PRT
<213> ORGANISM: Homo sapiens

<400> SEQUENCE: 66

Pro Gly Pro Lys Gly Ser Pro Gly Ser Val Gly Leu Lys
1               5                   10

<210> SEQ ID NO 67
<211> LENGTH: 12
<212> TYPE: PRT
<213> ORGANISM: Homo sapiens
<220> FEATURE:
<221> NAME/KEY: Hydroxyl group
<222> LOCATION: (5)..(5)
<223> OTHER INFORMATION: Hydroxyl group
<220> FEATURE:
<221> NAME/KEY: Hydroxyl group
<222> LOCATION: (11)..(11)
<223> OTHER INFORMATION: Hydroxyl group

<400> SEQUENCE: 67

Gly Leu Pro Gly Pro Pro Gly Pro Met Asp Pro Asn
1               5                   10

<210> SEQ ID NO 68
<211> LENGTH: 16
<212> TYPE: PRT
<213> ORGANISM: Homo sapiens
<220> FEATURE:
<221> NAME/KEY: Hydroxyl group
<222> LOCATION: (2)..(2)
<223> OTHER INFORMATION: Hydroxyl group
<220> FEATURE:
<221> NAME/KEY: Hydroxyl group
<222> LOCATION: (8)..(8)
<223> OTHER INFORMATION: Hydroxyl group
<220> FEATURE:
<221> NAME/KEY: Hydroxyl group
<222> LOCATION: (14)..(14)
<223> OTHER INFORMATION: Hydroxyl group

<400> SEQUENCE: 68
```

```
Ser Pro Gly Ser Asn Gly Ala Pro Gly Gln Arg Gly Glu Pro Gly Pro
1               5                   10                  15

<210> SEQ ID NO 69
<211> LENGTH: 15
<212> TYPE: PRT
<213> ORGANISM: Homo sapiens

<400> SEQUENCE: 69

Lys Leu Lys Lys Thr Pro Thr Glu Ala Pro Ala Asp Cys Arg Ala
1               5                   10                  15

<210> SEQ ID NO 70
<211> LENGTH: 20
<212> TYPE: PRT
<213> ORGANISM: Homo sapiens
<220> FEATURE:
<221> NAME/KEY: Hydroxyl group
<222> LOCATION: (3)..(3)
<223> OTHER INFORMATION: Hydroxyl group
<220> FEATURE:
<221> NAME/KEY: Hydroxyl group
<222> LOCATION: (8)..(8)
<223> OTHER INFORMATION: Hydroxyl group
<220> FEATURE:
<221> NAME/KEY: Hydroxyl group
<222> LOCATION: (9)..(9)
<223> OTHER INFORMATION: Hydroxyl group
<220> FEATURE:
<221> NAME/KEY: Hydroxyl group
<222> LOCATION: (20)..(20)
<223> OTHER INFORMATION: Hydroxyl group

<400> SEQUENCE: 70

Gly Leu Pro Gly Thr Gly Gly Pro Pro Gly Glu Asn Gly Lys Pro Gly
1               5                   10                  15

Glu Pro Gly Pro
            20

<210> SEQ ID NO 71
<211> LENGTH: 16
<212> TYPE: PRT
<213> ORGANISM: Homo sapiens
<220> FEATURE:
<221> NAME/KEY: Glycine-Glycine
<222> LOCATION: (9)..(9)
<223> OTHER INFORMATION: Glycine-Glycine dipeptide addition to the side
      chain epsilon amino group of lysine

<400> SEQUENCE: 71

Trp Gly Tyr His Gly Glu Gly Asn Lys Ser Leu Val Val Ala His Ala
1               5                   10                  15

<210> SEQ ID NO 72
<211> LENGTH: 25
<212> TYPE: PRT
<213> ORGANISM: Homo sapiens
<220> FEATURE:
<221> NAME/KEY: Hydroxyl group
<222> LOCATION: (3)..(3)
<223> OTHER INFORMATION: Hydroxyl group
<220> FEATURE:
<221> NAME/KEY: Hydroxyl group
<222> LOCATION: (15)..(15)
<223> OTHER INFORMATION: Hydroxyl group
<220> FEATURE:
<221> NAME/KEY: Hydroxyl group
<222> LOCATION: (18)..(18)
<223> OTHER INFORMATION: Hydroxyl group
<220> FEATURE:
<221> NAME/KEY: Hydroxyl group
<222> LOCATION: (24)..(24)
```

```
<223> OTHER INFORMATION: Hydroxyl group

<400> SEQUENCE: 72

Gly Ala Pro Gly Asn Asp Gly Ala Lys Gly Asp Ala Gly Ala Pro Gly
1               5                   10                  15

Ala Pro Gly Ser Gln Gly Ala Pro Gly
            20                  25

<210> SEQ ID NO 73
<211> LENGTH: 22
<212> TYPE: PRT
<213> ORGANISM: Homo sapiens
<220> FEATURE:
<221> NAME/KEY: Hydroxyl group
<222> LOCATION: (3)..(3)
<223> OTHER INFORMATION: Hydroxyl group
<220> FEATURE:
<221> NAME/KEY: Hydroxyl group
<222> LOCATION: (7)..(7)
<223> OTHER INFORMATION: Hydroxyl group
<220> FEATURE:
<221> NAME/KEY: Hydroxyl group
<222> LOCATION: (10)..(10)
<223> OTHER INFORMATION: Hydroxyl group

<400> SEQUENCE: 73

Pro Gly Pro Trp Gly Ala Pro Gly Leu Pro Gly Glu Lys Gly Asp His
1               5                   10                  15

Gly Phe Pro Gly Ser Ser
            20

<210> SEQ ID NO 74
<211> LENGTH: 23
<212> TYPE: PRT
<213> ORGANISM: Homo sapiens
<220> FEATURE:
<221> NAME/KEY: Hydroxyl group
<222> LOCATION: (7)..(7)
<223> OTHER INFORMATION: Hydroxyl group
<220> FEATURE:
<221> NAME/KEY: Hydroxyl group
<222> LOCATION: (20)..(20)
<223> OTHER INFORMATION: Hydroxyl group

<400> SEQUENCE: 74

Lys Asn Gly Glu Tyr Gly Pro Gln Gly Pro Pro Gly Pro Thr Gly Pro
1               5                   10                  15

Gly Gly Asp Lys Gly Asp Thr
            20

<210> SEQ ID NO 75
<211> LENGTH: 24
<212> TYPE: PRT
<213> ORGANISM: Homo sapiens
<220> FEATURE:
<221> NAME/KEY: Hydroxyl group
<222> LOCATION: (17)..(17)
<223> OTHER INFORMATION: Hydroxyl group
<220> FEATURE:
<221> NAME/KEY: Hydroxyl group
<222> LOCATION: (22)..(22)
<223> OTHER INFORMATION: Hydroxyl group

<400> SEQUENCE: 75

Pro Lys Gly Arg Gly Gly Pro Asn Gly Asp Pro Gly Pro Leu Gly Pro
1               5                   10                  15

Pro Gly Glu Lys Gly Lys Leu Gly
            20
```

-continued

<210> SEQ ID NO 76
<211> LENGTH: 21
<212> TYPE: PRT
<213> ORGANISM: Homo sapiens

<400> SEQUENCE: 76

Leu Ser Asp Pro Glu Gln Gly Val Glu Val Thr Gly Gln Tyr Glu Arg
1               5                   10                  15

Glu Lys Ala Gly Phe
            20

<210> SEQ ID NO 77
<211> LENGTH: 24
<212> TYPE: PRT
<213> ORGANISM: Homo sapiens
<220> FEATURE:
<221> NAME/KEY: Hydroxyl group
<222> LOCATION: (12)..(12)
<223> OTHER INFORMATION: Hydroxyl group
<220> FEATURE:
<221> NAME/KEY: Hydroxyl group
<222> LOCATION: (15)..(15)
<223> OTHER INFORMATION: Hydroxyl group
<220> FEATURE:
<221> NAME/KEY: Hydroxyl group
<222> LOCATION: (21)..(21)
<223> OTHER INFORMATION: Hydroxyl group

<400> SEQUENCE: 77

Gly Lys Asn Gly Asp Asp Gly Glu Ala Gly Lys Pro Gly Arg Pro Gly
1               5                   10                  15

Glu Arg Gly Pro Pro Gly Pro Gln
            20

<210> SEQ ID NO 78
<211> LENGTH: 20
<212> TYPE: PRT
<213> ORGANISM: Homo sapiens
<220> FEATURE:
<221> NAME/KEY: Hydroxyl group
<222> LOCATION: (16)..(16)
<223> OTHER INFORMATION: Hydroxyl group
<220> FEATURE:
<221> NAME/KEY: Hydroxyl group
<222> LOCATION: (17)..(17)
<223> OTHER INFORMATION: Hydroxyl group

<400> SEQUENCE: 78

Cys Gln Ala Ile Arg Glu Ala Tyr Leu Thr Gln Leu Met Ile Ile Lys
1               5                   10                  15

Asn Ser Thr Tyr
            20

<210> SEQ ID NO 79
<211> LENGTH: 36
<212> TYPE: PRT
<213> ORGANISM: Homo sapiens
<220> FEATURE:
<221> NAME/KEY: Hydroxyl group
<222> LOCATION: (6)..(6)
<223> OTHER INFORMATION: Hydroxyl group
<220> FEATURE:
<221> NAME/KEY: Hydroxyl group
<222> LOCATION: (7)..(7)
<223> OTHER INFORMATION: Hydroxyl group
<220> FEATURE:
<221> NAME/KEY: Hydroxyl group
<222> LOCATION: (16)..(16)
<223> OTHER INFORMATION: Hydroxyl group
<220> FEATURE:

```
<221> NAME/KEY: Hydroxyl group
<222> LOCATION: (19)..(19)
<223> OTHER INFORMATION: Hydroxyl group
<220> FEATURE:
<221> NAME/KEY: Hydroxyl group
<222> LOCATION: (22)..(22)
<223> OTHER INFORMATION: Hydroxyl group
<220> FEATURE:
<221> NAME/KEY: Hydroxyl group
<222> LOCATION: (27)..(27)
<223> OTHER INFORMATION: Hydroxyl group
<220> FEATURE:
<221> NAME/KEY: Hydroxyl group
<222> LOCATION: (28)..(28)
<223> OTHER INFORMATION: Hydroxyl group

<400> SEQUENCE: 79

Ala Gly Pro Pro Gly Pro Pro Gly Pro Pro Gly Thr Ser Gly His Pro
1               5                   10                  15

Gly Ser Pro Gly Ser Pro Gly Tyr Gln Gly Pro Pro Gly Glu Pro Gly
                20                  25                  30

Gln Ala Gly Pro
            35

<210> SEQ ID NO 80
<211> LENGTH: 16
<212> TYPE: PRT
<213> ORGANISM: Homo sapiens

<400> SEQUENCE: 80

Ala Asp Ser Gly Glu Gly Asp Phe Leu Ala Glu Gly Gly Gly Val Arg
1               5                   10                  15

<210> SEQ ID NO 81
<211> LENGTH: 16
<212> TYPE: PRT
<213> ORGANISM: Homo sapiens

<400> SEQUENCE: 81

Ala Asp Ser Gly Glu Gly Asp Phe Leu Ala Glu Gly Gly Gly Val Arg
1               5                   10                  15

<210> SEQ ID NO 82
<211> LENGTH: 27
<212> TYPE: PRT
<213> ORGANISM: Homo sapiens

<400> SEQUENCE: 82

Met Ala Asp Glu Ala Gly Ser Glu Ala Asp His Glu Gly Thr His Ser
1               5                   10                  15

Thr Lys Arg Gly His Ala Lys Ser Arg Pro Val
                20                  25

<210> SEQ ID NO 83
<211> LENGTH: 27
<212> TYPE: PRT
<213> ORGANISM: Homo sapiens
<220> FEATURE:
<221> NAME/KEY: Oxidation
<222> LOCATION: (1)..(1)
<223> OTHER INFORMATION: Oxidation of sulfur on methionine side chain

<400> SEQUENCE: 83

Met Ala Asp Glu Ala Gly Ser Glu Ala Asp His Glu Gly Thr His Ser
1               5                   10                  15

Thr Lys Arg Gly His Ala Lys Ser Arg Pro Val
                20                  25
```

<210> SEQ ID NO 84
<211> LENGTH: 7
<212> TYPE: PRT
<213> ORGANISM: Homo sapiens

<400> SEQUENCE: 84

Arg Pro Pro Gly Phe Ser Pro
1               5

<210> SEQ ID NO 85
<211> LENGTH: 8
<212> TYPE: PRT
<213> ORGANISM: Homo sapiens

<400> SEQUENCE: 85

Arg Pro Pro Gly Phe Ser Pro Phe
1               5

<210> SEQ ID NO 86
<211> LENGTH: 8
<212> TYPE: PRT
<213> ORGANISM: Homo sapiens
<220> FEATURE:
<221> NAME/KEY: Hydroxyl group
<222> LOCATION: (3)..(3)
<223> OTHER INFORMATION: Hydroxyl group

<400> SEQUENCE: 86

Arg Pro Pro Gly Phe Ser Pro Phe
1               5

<210> SEQ ID NO 87
<211> LENGTH: 8
<212> TYPE: PRT
<213> ORGANISM: Homo sapiens
<220> FEATURE:
<221> NAME/KEY: Hydroxyl group
<222> LOCATION: (7)..(7)
<223> OTHER INFORMATION: Hydroxyl group

<400> SEQUENCE: 87

Arg Pro Pro Gly Phe Ser Pro Phe
1               5

<210> SEQ ID NO 88
<211> LENGTH: 9
<212> TYPE: PRT
<213> ORGANISM: Homo sapiens

<400> SEQUENCE: 88

Arg Pro Pro Gly Phe Ser Pro Phe Arg
1               5

<210> SEQ ID NO 89
<211> LENGTH: 9
<212> TYPE: PRT
<213> ORGANISM: Homo sapiens
<220> FEATURE:
<221> NAME/KEY: Hydroxyl group
<222> LOCATION: (3)..(3)
<223> OTHER INFORMATION: Hydroxyl group
<220> FEATURE:
<221> NAME/KEY: Hydroxyl group
<222> LOCATION: (7)..(7)
<223> OTHER INFORMATION: Hydroxyl group

<400> SEQUENCE: 89

```
Arg Pro Pro Gly Phe Ser Pro Phe Arg
1               5

<210> SEQ ID NO 90
<211> LENGTH: 8
<212> TYPE: PRT
<213> ORGANISM: Homo sapiens

<400> SEQUENCE: 90

Asp Trp Gly His Glu Lys Gln Arg
1               5

<210> SEQ ID NO 91
<211> LENGTH: 17
<212> TYPE: PRT
<213> ORGANISM: Homo sapiens

<400> SEQUENCE: 91

Asn Leu Gly His Gly His Lys His Glu Arg Asp Gln Gly His Gly His
1               5                   10                  15

Gln

<210> SEQ ID NO 92
<211> LENGTH: 9
<212> TYPE: PRT
<213> ORGANISM: Homo sapiens

<400> SEQUENCE: 92

Asn Phe Arg Pro Gly Val Leu Ser Ser
1               5

<210> SEQ ID NO 93
<211> LENGTH: 17
<212> TYPE: PRT
<213> ORGANISM: Homo sapiens

<400> SEQUENCE: 93

Gly Leu Pro Gly Pro Pro Asp Val Pro Asp His Ala Ala Tyr His Pro
1               5                   10                  15

Phe

<210> SEQ ID NO 94
<211> LENGTH: 15
<212> TYPE: PRT
<213> ORGANISM: Homo sapiens

<400> SEQUENCE: 94

Gly Pro Pro Asp Val Pro Asp His Ala Ala Tyr His Pro Phe Arg
1               5                   10                  15

<210> SEQ ID NO 95
<211> LENGTH: 7
<212> TYPE: PRT
<213> ORGANISM: Homo sapiens

<400> SEQUENCE: 95

His Ala Ala Tyr His Pro Phe
1               5

<210> SEQ ID NO 96
<211> LENGTH: 9
<212> TYPE: PRT
<213> ORGANISM: Homo sapiens
<220> FEATURE:
<221> NAME/KEY: Optional carboxylation
```

```
<222> LOCATION: (2)..(2)
<223> OTHER INFORMATION: Optional carboxylation of glutamic acid side
      chain
<220> FEATURE:
<221> NAME/KEY: Optional carboxylation
<222> LOCATION: (5)..(5)
<223> OTHER INFORMATION: Optional carboxylation of glutamic acid side
      chain

<400> SEQUENCE: 96

Asp Glu Gly Ala Glu Pro Leu Lys Gln
1               5

<210> SEQ ID NO 97
<211> LENGTH: 12
<212> TYPE: PRT
<213> ORGANISM: Homo sapiens

<400> SEQUENCE: 97

Asn Gly Phe Lys Ser His Ala Leu Gln Leu Asn Asn
1               5                   10

<210> SEQ ID NO 98
<211> LENGTH: 9
<212> TYPE: PRT
<213> ORGANISM: Homo sapiens
<220> FEATURE:
<221> NAME/KEY: Carboxylation
<222> LOCATION: (1)..(1)
<223> OTHER INFORMATION: Gamma carboxylation of glutamic acid side chain

<400> SEQUENCE: 98

Glu Pro Pro Thr Ser Ala Ser Ile Leu
1               5

<210> SEQ ID NO 99
<211> LENGTH: 10
<212> TYPE: PRT
<213> ORGANISM: Homo sapiens

<400> SEQUENCE: 99

Ile Cys His Thr Gly His Glu Gln Ala Gly
1               5                   10

<210> SEQ ID NO 100
<211> LENGTH: 11
<212> TYPE: PRT
<213> ORGANISM: Homo sapiens

<400> SEQUENCE: 100

Ile Cys His Thr Gly His Glu Gln Ala Gly Arg
1               5                   10

<210> SEQ ID NO 101
<211> LENGTH: 9
<212> TYPE: PRT
<213> ORGANISM: Homo sapiens

<400> SEQUENCE: 101

Asp Asp Met Ser Gly Asp Glu Lys Gln
1               5

<210> SEQ ID NO 102
<211> LENGTH: 8
<212> TYPE: PRT
<213> ORGANISM: Homo sapiens
<220> FEATURE:
<221> NAME/KEY: Carboxylation
```

```
<222> LOCATION: (3)..(3)
<223> OTHER INFORMATION: Gamma carboxylation of glutamic acid side chain

<400> SEQUENCE: 102

Ile Arg Glu Gly His Glu Lys Gln
1               5

<210> SEQ ID NO 103
<211> LENGTH: 8
<212> TYPE: PRT
<213> ORGANISM: Homo sapiens
<220> FEATURE:
<221> NAME/KEY: Carboxylation
<222> LOCATION: (6)..(6)
<223> OTHER INFORMATION: Gamma carboxylation of glutamic acid side chain

<400> SEQUENCE: 103

Ile Arg Glu Gly His Glu Lys Gln
1               5

<210> SEQ ID NO 104
<211> LENGTH: 9
<212> TYPE: PRT
<213> ORGANISM: Homo sapiens

<400> SEQUENCE: 104

Met Ala Glu Ala Ser Glu Asp Ser Pro
1               5

<210> SEQ ID NO 105
<211> LENGTH: 12
<212> TYPE: PRT
<213> ORGANISM: Homo sapiens
<220> FEATURE:
<221> NAME/KEY: Optional hydroxyl group
<222> LOCATION: (3)..(3)
<223> OTHER INFORMATION: Optional hydroxyl group
<220> FEATURE:
<221> NAME/KEY: Optional hydroxyl group
<222> LOCATION: (10)..(10)
<223> OTHER INFORMATION: Optional hydroxyl group

<400> SEQUENCE: 105

Arg Ser Pro Ser Ser Leu Leu His Asp Pro Ala Leu
1               5                   10

<210> SEQ ID NO 106
<211> LENGTH: 13
<212> TYPE: PRT
<213> ORGANISM: Homo sapiens
<220> FEATURE:
<221> NAME/KEY: Optional hydroxyl group
<222> LOCATION: (1)..(1)
<223> OTHER INFORMATION: Optional hydroxyl group
<220> FEATURE:
<221> NAME/KEY: Optional hydroxyl group
<222> LOCATION: (3)..(3)
<223> OTHER INFORMATION: Optional hydroxyl group
<220> FEATURE:
<221> NAME/KEY: Optional hydroxyl group
<222> LOCATION: (5)..(5)
<223> OTHER INFORMATION: Optional hydroxyl group

<400> SEQUENCE: 106

Pro Thr Pro Arg Pro Arg Arg Met Lys Lys Asp Glu Ser
1               5                   10

<210> SEQ ID NO 107
<211> LENGTH: 8
<212> TYPE: PRT
```

```
<213> ORGANISM: Homo sapiens

<400> SEQUENCE: 107

Val Ser Val His Pro Asp Tyr Arg
1               5

<210> SEQ ID NO 108
<211> LENGTH: 11
<212> TYPE: PRT
<213> ORGANISM: Homo sapiens
<220> FEATURE:
<221> NAME/KEY: Carboxylation
<222> LOCATION: (4)..(4)
<223> OTHER INFORMATION: Gamma carboxylation of glutamic acid side chain
<220> FEATURE:
<221> NAME/KEY: Hydroxyl group
<222> LOCATION: (10)..(10)
<223> OTHER INFORMATION: Hydroxyl group

<400> SEQUENCE: 108

Thr Asp Ser Glu Ser Ser Ala Ser Leu Pro Arg
1               5                   10

<210> SEQ ID NO 109
<211> LENGTH: 16
<212> TYPE: PRT
<213> ORGANISM: Homo sapiens
<220> FEATURE:
<221> NAME/KEY: Optional hydroxyl group
<222> LOCATION: (11)..(11)
<223> OTHER INFORMATION: Optional hydroxyl group
<220> FEATURE:
<221> NAME/KEY: Optional hydroxyl group
<222> LOCATION: (12)..(12)
<223> OTHER INFORMATION: Optional hydroxyl group
<220> FEATURE:
<221> NAME/KEY: Optional hydroxyl group
<222> LOCATION: (13)..(13)
<223> OTHER INFORMATION: Optional hydroxyl group

<400> SEQUENCE: 109

Arg Arg Thr Gln Glu Gly Gly Arg Gly Asp Pro Pro Pro Ala Gly Arg
1               5                   10                  15

<210> SEQ ID NO 110
<211> LENGTH: 8
<212> TYPE: PRT
<213> ORGANISM: Homo sapiens

<400> SEQUENCE: 110

Asp His Pro Asn Glu Glu Gln Gln
1               5

<210> SEQ ID NO 111
<211> LENGTH: 8
<212> TYPE: PRT
<213> ORGANISM: Homo sapiens
<220> FEATURE:
<221> NAME/KEY: Optional carboxylation
<222> LOCATION: (5)..(5)
<223> OTHER INFORMATION: Optional carboxylation of glutamic acid side
      chain
<220> FEATURE:
<221> NAME/KEY: Optional carboxylation
<222> LOCATION: (6)..(6)
<223> OTHER INFORMATION: Optional carboxylation of glutamic acid side
      chain

<400> SEQUENCE: 111

Asp His Pro Asn Glu Glu Gln Gln
1               5
```

```
<210> SEQ ID NO 112
<211> LENGTH: 9
<212> TYPE: PRT
<213> ORGANISM: Homo sapiens
<220> FEATURE:
<221> NAME/KEY: Hydroxyl group
<222> LOCATION: (8)..(8)
<223> OTHER INFORMATION: Hydroxyl group

<400> SEQUENCE: 112

Gly Leu Glu Ser Gly Asp Ile Pro Ser
 1               5

<210> SEQ ID NO 113
<211> LENGTH: 7
<212> TYPE: PRT
<213> ORGANISM: Homo sapiens

<400> SEQUENCE: 113

Pro His Asp Ser Gly Gln Gln
 1               5

<210> SEQ ID NO 114
<211> LENGTH: 7
<212> TYPE: PRT
<213> ORGANISM: Homo sapiens
<220> FEATURE:
<221> NAME/KEY: Carboxylation
<222> LOCATION: (2)..(2)
<223> OTHER INFORMATION: Gamma carboxylation of glutamic acid side chain
<220> FEATURE:
<221> NAME/KEY: Hydroxyl group
<222> LOCATION: (5)..(5)
<223> OTHER INFORMATION: Hydroxyl group

<400> SEQUENCE: 114

Arg Glu Thr Ser Pro Asn Arg
 1               5

<210> SEQ ID NO 115
<211> LENGTH: 13
<212> TYPE: PRT
<213> ORGANISM: Homo sapiens
<220> FEATURE:
<221> NAME/KEY: Optional hydroxyl group
<222> LOCATION: (5)..(5)
<223> OTHER INFORMATION: Optional hydroxyl group
<220> FEATURE:
<221> NAME/KEY: Optional hydroxyl group
<222> LOCATION: (6)..(6)
<223> OTHER INFORMATION: Optional hydroxyl group

<400> SEQUENCE: 115

His Arg Ser His Pro Pro Gly Trp Ala Ser Gly Ala Arg
 1               5                  10

<210> SEQ ID NO 116
<211> LENGTH: 10
<212> TYPE: PRT
<213> ORGANISM: Homo sapiens
<220> FEATURE:
<221> NAME/KEY: Carboxylation
<222> LOCATION: (4)..(4)
<223> OTHER INFORMATION: Gamma carboxylation of glutamic acid side chain
<220> FEATURE:
<221> NAME/KEY: Hydroxyl group
<222> LOCATION: (5)..(5)
<223> OTHER INFORMATION: Hydroxyl group

<400> SEQUENCE: 116
```

```
Asn Gly Ala Glu Pro Ser Arg Ala Val Gly
1               5                   10

<210> SEQ ID NO 117
<211> LENGTH: 15
<212> TYPE: PRT
<213> ORGANISM: Homo sapiens
<220> FEATURE:
<221> NAME/KEY: Hydroxyl group
<222> LOCATION: (7)..(7)
<223> OTHER INFORMATION: Hydroxyl group
<220> FEATURE:
<221> NAME/KEY: Optional carboxylation
<222> LOCATION: (9)..(9)
<223> OTHER INFORMATION: Optional carboxylation of glutamic acid side
      chain
<220> FEATURE:
<221> NAME/KEY: Optional carboxylation
<222> LOCATION: (10)..(10)
<223> OTHER INFORMATION: Optional carboxylation of glutamic acid side
      chain
<220> FEATURE:
<221> NAME/KEY: Hydroxyl group
<222> LOCATION: (13)..(13)
<223> OTHER INFORMATION: Hydroxyl group

<400> SEQUENCE: 117

Arg Thr Asp Glu Val Leu Pro Glu Glu Ala Ala Pro Arg Arg Lys
1               5                   10                  15

<210> SEQ ID NO 118
<211> LENGTH: 15
<212> TYPE: PRT
<213> ORGANISM: Homo sapiens

<400> SEQUENCE: 118

Tyr Glu Asn Gly Glu Tyr Ile Ile Arg Gln Gly Ala Arg Gly Asp
1               5                   10                  15
```